US010113205B2

(12) United States Patent
Tyler

(10) Patent No.: US 10,113,205 B2
(45) Date of Patent: Oct. 30, 2018

(54) COMPOSITIONS TO DETECT SEASONAL H1 INFLUENZA A VIRUS NUCLEIC ACIDS

(71) Applicant: GEN-PROBE INCORPORATED, San Diego, CA (US)

(72) Inventor: Ejan Tyler, San Diego, CA (US)

(73) Assignee: GEN-PROBE INCORPORATED, San Diego, CA (US)

( * ) Notice: Subject to any disclaimer, the term of this patent is extended or adjusted under 35 U.S.C. 154(b) by 373 days.

(21) Appl. No.: 14/990,015

(22) Filed: Jan. 7, 2016

(65) Prior Publication Data

US 2016/0130672 A1 May 12, 2016

Related U.S. Application Data

(62) Division of application No. 13/809,854, filed as application No. PCT/US2011/043736 on Jul. 12, 2011, now Pat. No. 9,234,249.

(60) Provisional application No. 61/363,628, filed on Jul. 12, 2010.

(51) Int. Cl.
*C12P 19/34* (2006.01)
*C12Q 1/70* (2006.01)
*C12Q 1/6851* (2018.01)

(52) U.S. Cl.
CPC .......... *C12Q 1/701* (2013.01); *C12Q 1/6851* (2013.01); *C12Q 2600/16* (2013.01)

(58) Field of Classification Search
None
See application file for complete search history.

(56) References Cited

U.S. PATENT DOCUMENTS

2006/0160759 A1 7/2006 Chen et al.
2009/0111089 A1 4/2009 Lindstrom et al.

FOREIGN PATENT DOCUMENTS

WO 2009/151407 A2 12/2009

OTHER PUBLICATIONS

Rychlik et al., Nucleic Acids Research 17(21), 8543-8551 (1989).*

Beck et al., "Development of a rapid automated influenza A, influenza B, and respiratory syncytial virus A/B multiplex real-time RT-PCR assay and its use during the 2009 H1N1 swine-origin influenza virus epidemic in Milwaukee, Wisconsin," J Mol Diagn. Jan. 2010, pp. 74-81, vol. 12, No. 1. doi: 10.2353/jmoldx.2010.090095. Epub Dec. 3, 2009.

Bose et al., "Rapid Semiautomated Subtyping of Influenza Virus Species during the 2009 Swine Origin Influenza A H1N1 Virus Epidemic in Milwaukee, Wisconsin," Journal of Clinical Microbiology, Sep. 2009, pp. 2779-2786, vol. 47, No. 9, American Society for Microbiology, Washington D.C., US.

Carr et al., "Development of a real-time RT-PCR for the detection of Swine-lineage Influenza A (H1N1) virus infections," Journal of Clinical Virology, 2009, pp. 196-199, vol. 45, Elsevier B.V., NL.

Chang et al., "Development of Multiplex RT-PCR Assays for Rapid Detection and Subtyping of Influenza Type A Viruses from Clinical Specimens," J. Microbiol. Biotechnol., 2008, pp. 1164-1169, vol. 18, No. 6, The Korean Society for Microbiology and Biotechnology, Seoul, Korea.

Chiou et al., "Detection of pandemic (H1N1) 2009 influenza virus by allele discrimination," Clinica Chimica Acta, 2010, pp. 1080-1083, vol. 411, Elsevier B.V., NL.

Deyde et al. "Genomic Signature-Based Identification of Influenza A Viruses Using RT-PCR/Electro-Spray Ionization Mass Spectrometry (ESI-MS) Technology," PLoS One, 2010, Oct. 12, vol. 5, No. 10, e13293, doi:10.1371/journal.pone.0013293.

Di Trani et al. "A sensitive one-step real-time PCR for detection of avian influenza viruses using a MGB probe and an internal positive control," BMC Infectious Diseases, 2006, vol. 6, No. 87, Di Trani et al, licensee BioMed Central Ltd., London, UK, doi:10.1186/1471-2334-6-87.

Dong et al., "Detection of human novel influenza A (H1N1) viruses using multi-fluorescent real-time RT-PCR," Virus Research, 2010, pp. 85-90, vol. 147, Elsevier B.V., NL.

Ellis et al., "Evaluation of four real-time PCR assays for detection of influenza A(H1N1) v viruses," Eurosurveillance, Jun. 4, 2009, vol. 14, No. 22, European Centre for Disease Prevention and Control (ECDC), Stockholm, Sweden. Available online: http://www.eurosurveillance.org/ViewArticle.aspx?ArticleId=19230.

Ellis et al., "Chapter 10. Simultaneous Molecular Detection and Confirmation of Influenza AH5, with Internal Control," In: Stephenson, J. and Warnes, A. eds. 2010. Diagnostic Virology Protocols. Secaucus, pp. 161-181, Springer Science +Business Media, LLC., New Jersy, US. doi:10.1007/978-1-60761-817-1_10.

Garten et al., "Antigenic and Genetic Characteristics of Swine-Origin 2009 A(H1N1) Influenza Viruses Circulating in Humans," Science, Jul. 10, 2009, pp. 197-201, vol. 325, DOI: 10.1126/science.1176225, American Association for the Advancement of Science, Washington DC, US.

(Continued)

*Primary Examiner* — Kenneth R Horlick
(74) *Attorney, Agent, or Firm* — Jeffrey E. Landes

(57) ABSTRACT

Methods for detecting the presence or absence of the swine H1N1 influenza A virus, seasonal H1 influenza A virus and/or seasonal H3 influenza A virus nucleic acids in biological samples are disclosed. Compositions that are target-specific nucleic acid sequences and kits comprising target-specific nucleic acid oligomers for amplifying in vitro the swine H1N1 influenza A virus, seasonal H1 influenza A virus and/or seasonal H3 influenza A virus nucleic acid and detecting amplified nucleic acid sequences are disclosed.

9 Claims, No Drawings

Specification includes a Sequence Listing.

(56) References Cited

OTHER PUBLICATIONS

Ge et al., "Detection of novel swine origin influenza A virus (H1N1) by real-time nucleic acid sequence-based amplification," Journal of Virological Methods, 2010, pp. 495-497, vol. 163, Elsevier B.V., NL.
Ginocchio et al., "Evaluation of multiple test methods for the detection of the novel 2009 influenza A (H1N1) during the New York City outbreak," Journal of Clinical Virology, 2009, pp. 191-195, vol. 45, Elsevier B.V., NL.
Gu et al. "Rapid and specific detection of H3 swine influenza virus using reverse transcription loop-mediated isothermal amplification method," Journal of Applied Microbiology, Apr. 2010, pp. 1145-1154, vol. 108, No. 4, The Authors. Journal compilation and The Society for Applied Microbiology, doi: 10.1111/j.1365-2672.2009.04520.x.
Hall et al., "Rapid Method to Support Diagnosis of Swine Origin Influenza Virus Infection by Sequencing of Real-Time PCR Amplicons from Diagnostic Assays," Journal of Clinical Microbiology, Sep. 2009, p. 3053-3054, vol. 47, No. 9, American Society for Microbiology (ASM), Washington D.C., US. doi:10.1128/JCM.01000-09.
Harmon et al., "A matrix gene-based multiplex real-time RT-PCR for detection and differentiation of 2009 pandemic H1N1 and other influenza A viruses in North America," Influenza Other Respi Viruses, Nov. 2010; pp. 405-410, vol. 4, No. 6, Blackwell Publishing Ltd., Oxford, UK, doi: 10.1111/j.1750-2659.2010.00153.x.
He et al., "Rapid Multiplex Reverse Transcription-PCR Typing of Influenza A and B Virus, and Subtyping of Influenza A Virus into H1, 2, 3, 5, 7, 9, N1 (Human), N1 (Animal), N2, and N7, Including Typing of Novel Swine Origin Influenza A (H1N1) Virus, during the 2009 Outbreak in Milwaukee, Wisconsin," Journal of Clinical Microbiology, Sep. 2009, pp. 2772-2778, vol. 47, No. 9, American Society for Microbiology, Washington D.C., US.
Hiromoto et al., "Real-time reverse transcription-PCR assay for differentiating the Pandemic H1N1 2009 influenza virus from swine influenza viruses," Journal of Virological Methods, 2010, pp. 169-172, vol. 170, Elsevier B.V., NL.
Hopkins et al., "Using the full spectral capacity (six channels) of a real-time PCR instrument can simplify diagnostic laboratory screening and typing protocols for pandemic H1N1 influenza," Influenza and Other Respiratory Viruses Mar. 2011, pp. 110-114, vol. 5, No. 2, Blackwell Publishing Ltd, Oxford, UK, DOI: 10.1111/j.1750-2659.2010.00178.x.
Hurt et al., "Performance of six influenza rapid tests in detecting human influenza in clinical specimens," Journal of Clinical Virology, 2007, pp. 132-135, vol. 39, Elsevier B.V., NL.
Influenza A H1N1 (2009) [package insert]. Cypress, CA: Focus Diagnostics; 2009.
International Preliminary Report on Patentability, International Patent Application No. PCT/US2011/043736, dated Jan. 15, 2013.
International Search Report, International Patent Application No. PCT/US2011/043736, dated Apr. 24, 2012.
Jiang et al., "Development of a real-time RT-PCR assay for a novel influenza A (H1N1) virus," Journal of Virological Methods, 2010, pp. 470-473, vol. 162, Elsevier B.V., NL.
Jindal et al., "Amplification of four genes of influenza A viruses using a degenerate primer set in a one step RT-PCR method," Journal of Virological Methods, 2009, pp. 163-166, vol. 160, Elsevier B.V., NL.
Kang et al., "Subtype identification of the novel A H1N1 and other human influenza A viruses using an oligonucleotide microarray," Arch. Virol., 2010, pp. 55-61, vol. 155, Springer-Verlag, Paris, France, doi: 10.1007/s00705-009-0545-z.
Kao et al., "Multiplexed detection and differentiation of the DNA strains for influenza A (H1N1 2009) using a silicon-based microfluidic system," Biosensors and Bioelectronics, 2-11, pp. 2006-2011, vol. 26, Elsevier B.V., NL.
Kaul et al., "Influenza A Subtyping—Seasonal H1N1, H3N2, and the Appearance of Novel H1N1," Journal of Molecular Diagnostics, Sep. 2010, pp. 664-669, vol. 12, No. 5, American Society for Investigative Pathology and the Association for Molecular Pathology, Bethesda, MD, US, DOI: 10.2353/jmoldx.2010.090225.
Lalle et al., "Design and clinical application of a molecular method for detection and typing of the influenza A/H1N1pdm virus," Journal of Virological Methods, 2010, pp. 486-488, vol. 163, Elsevier B.V., NL.
Lam et al. "Development and Comparison of Molecular Assays for the Rapid Detection of the Pandemic Influenza A (H1N1) 2009 Virus." Journal of Medical Virology, Apr. 1, 2010, pp. 675-683, vol. 82, No. 4, Wiley-Liss, Inc., Wilmington, DE, US.
Lau et al., "Confirmation of the First Hong Kong Case of Human Infection by Novel Swine Origin Influenza A (H1N1) Virus Diagnosed Using Ultrarapid, Real-Time Reverse Transcriptase PCR," Journal of Clinical Microbiology, Jul. 2009, p. 2344-2346, vol. 47, No. 7, American Society for Microbiology, Washington D.C., US. doi:10.1128/JCM.00924-09.
LeBlanc et al., "Switching Gears for an Influenza Pandemic: Validation of a Duplex Reverse Transcriptase PCR Assay for Simultaneous Detection and Confirmatory Identification of Pandemic (H1N1) 2009 Influenza Virus," Journal of Clinical Microbiology, Dec. 2009, p. 3805-3813, vol. 47, No. 12, American Society for Microbiology, Washington D.C., US, doi:10.1128/JCM.01344-09.
Lee et al., "One-step multiplex RT-PCR for detection and subtyping of swine influenza H1, H3, N1, N2 viruses in clinical samples using a dual priming oligonucleotide (DPO) system," Journal of Virological Methods, 2008, pp. 30-34, vol. 151, Elsevier B.V., NL.
Lee et al., "Diagnostic Testing for Pandemic Influenza in Singapore. A Novel Dual-Gene Quantitative Real-Time RT-PCR for the Detection of Influenza A/H1N1/2009," Journal of Molecular Diagnostics, Sep. 2010, pp. 636-643, vol. 12, No. 5, American Society for Investigative Pathology and the Association for Molecular Pathology, Bethesda, MD, US.
Liu et al., "A SYBR Green I real-time RT-PCR assay for detection and differentiation of influenza A(H1N1) virus in swine populations," J. Virol. Methods (2009), doi:10.1016/j.jviromet.2009.07.035.
Lorusso et al., "One-step real-time RT-PCR for pandemic influenza A virus (H1N1) 2009 matrix gene detection in swine samples," Journal of Virological Methods, 2010, pp. 83-87, vol. 164, Elsevier B.V., NL.
Ma et al., "Rapid detection of the pandemic 2009 H1N1 virus M gene by real-time and gel-based RT-PCR assays," Influenza Other Respi Viruses, Nov. 2010, pp. 397-403, vol. 4, No. 6, Blackwell Publishing Ltd., Oxford, UK, doi: 10.1111/j.1750-2659.2010.00180.x.
Mahoney, "Nucleic acid amplification-based diagnosis of respiratory virus infections," Expert Rev. Anti Infect. Ther. 2010, pp. 1273-1292, vol. 8 , No. 11, Expert Reviews Ltd., London, UK, DOI: 10.1586/ERI.10.121.
Mak et al "Rapid genotyping of swine influenza viruses," Emerging Infectious Diseases, Apr. 2011, pp. 691-694, vol. 17, No. 4, www.cdc/gov/eid, http://dx.doi.org/10.3201/eid1704101726.
Nagarajan et al., "Single-step multiplex conventional and real-time reverse transcription polymerase chain reaction assays for simultaneous detection and subtype differentiation of Influenza A virus in swine," J Vet Diagn Invest., May 2010, pp. 402-408, vol. 22, No. 3, Sage Publications, Thousand Oaks, US, http://vdi.sagepub.com/content/22/3/402.
Nagy et al., "Development and evaluation of a one-step real-time RT-PCR assay for universal detection of influenza A viruses from avian and mammal species," Arch. Virol., 2010, pp. 665-673, vol. 155, Springer-Verlag, Paris, France.
Ninove et al., "A Simple Method for Molecular Detection of Swine-Origin and Human-Origin Influenza A Virus," Vector-Borne and Zoonotic Diseases, Apr. 2010, pp. 237-240, vol. 10, No. 3, Mary Ann Liebert, Inc., New Rochelle, NY, US. DOI: 10.1089=vbz.2009.0110.
Novel Swine-Origin Influenza A (H1N1) Virus Investigation Team, Dawood et al., "Emergence of a novel swine-origin influenza A

(56) References Cited

OTHER PUBLICATIONS (H1N1) virus in humans," N Engl J Med., Jun. 18, 2009, pp. 2605-2615, vol. 360, No. 25, doi: 10.1056/NEJMoa0903810. Epub May 7, 2009.
Pannging et al., "Singleplex real-time RT-PCR for detection of influenza A virus and simultaneous differentiation of A/H1N1v and evaluation of the RealStar influenza kit," Journal of Clinical Virology, 2011, pp. 171-174, vol. 50, Elsevier B.V., NL.
Phipps et al., "Genetic subtyping of influenza A viruses using RT-PCR with a single set of primers based on conserved sequences within the HA2 coding region," Journal of Virological Methods, 2004, pp. 119-122, vol. 122, Elsevier B.V., NL.
Poon et al., "Molecular Detection of a Novel Human Influenza (H1N1) of Pandemic Potential by Conventional and Real-Time Quantitative RT-PCR Assays," Clinical Chemistry, Aug. 2009, pp. 1555-1558, vol. 55, No. 8, The American Association for Clinical Chemistry, Washington D.C., US.
Poon et al., "Rapid Detection of Reassortment of Pandemic H1N1/2009 Influenza Virus," Clinical Chemistry, Aug. 2010, pp. 1340-1344, vol. 56, No. 8, The American Association for Clinical Chemistry, Washington D.C., US.
Qin et al. "Development of single-tube multiplex real-time PCR for simultaneous detection of novel influenza A H1N1 and human seasonal influenza A H1N1 and H3N2 virus", Bing Du Xue Bao = Chinese Journal of Virology/Mar. 2010, 20480637, pp. 97-102, vol. 26, No. 2. Abstract.
Qin et al. "Detection of pandemic influenza A H1N1 virus by multiplex reverse transcription-PCR with a GeXP analyzer," Journal of Virological Methods, May 7, 2010, pp. 255-258, vol. 168, No. 1-2, Elsevier B.V., NL.
Quest Diagnostics. FDA Grants First Authorization of a Commercial 2009 H1N1 Flu Test for use [press release]. Jul. 24, 2009, Madison, New Jersey, US.
ResSeq Accession CY_045552.1, GI:257127186, NCBI GenBank, 2011, http://www.ncbi.nlm.nih.gov/nuccore/CY045552.
ResSeq Accession CY_045560.1, GI:257127205, NCBI GenBank, 2011, http://www.ncbi.nlm.nih.gov/nuccore/CY045560.
ResSeq Accession GQ_150329.1, GI:237624329, NCBI GenBank, http://www.ncbi.nlm.nih.gov/nuccore/GQ150329.
ResSeq Accession GQ_229302.1, GI:239618815, NCBI GenBank, 2009, http://www.ncbi.nlm.nih.gov/nuccore/GQ229302.
ResSeq Accession GQ_229342.1, GI:239618825, NCBI GenBank, 2009, http://www.ncbi.nlm.nih.gov/nuccore/GQ229342.
ResSeq Accession GQ_478577.1, GI:255988296, NCBI GenBank, http://www.ncbi.nlm.nih.gov/nuccore/GQ478577.
ResSeq Accession GQ_478578.1, GI:255988298, NCBI GenBank, http://www.ncbi.nlm.nih.gov/nuccore/GQ478578.
ResSeq Accession GQ_478579.1, GI:255988300, NCBI GenBank, http://www.ncbi.nlm.nih.gov/nuccore/GQ478579.
ResSeq Accession GQ_478580.1, GI:255988302, NCBI GenBank, http://www.ncbi.nlm.nih.gov/nuccore/GQ478580.
ResSeq Accession GQ_478581.1, GI:255988304, NCBI GenBank, http://www.ncbi.nlm.nih.gov/nuccore/GQ478581.
ResSeq Accession GQ_478582.1, GI:255988306, NCBI GenBank, http://www.ncbi.nlm.nih.gov/nuccore/GQ478582.
ResSeq Accession GQ_478583.1, GI:255988308, NCBI GenBank, http://www.ncbi.nlm.nih.gov/nuccore/GQ478583.
Ryabinin et al., "Universal Oligonucleotide Microarray for Sub-Typing of Influenza A Virus," 2011, PLoS ONE, vol. 6, No. 4, e17529. doi:10.1371/journal.pone.0017529.
Shin et al, "One-Step Multiplex Reverse-Transcriptase PCR for Detecting Pandemic (H1N1) 2009 Influenza Virus," J. Vet. Med. Sci., 2011, pp. 55-63, vol. 73, No. 1, Japanese Society of Veterinary Science, Tokyo, Japan.
Shu et al., "Design and Performance of the CDC Real-Time Reverse Transcriptase PCR Swine Flu Panel for Detection of 2009 A (H1N1) Pandemic Influenza Virus," Journal of Clinical Microbiology, Jul. 2011, pp. 2614-2619, vol. 49, No. 7, American Society for Microbiology, Washington D.C., US.
Slomka et al., "Real time reverse transcription (RRT)-polymerase chain reaction (PCR) methods for detection of pandemic (H1N1) 2009 influenza virus and European swine influenza A virus infections in pigs," Influenza and Other Respiratory Viruses, Sep. 2010, pp. 277-293, vol. 4, Issue 5, Blackwell Publishing Ltd, Oxford, UK, DOI: 10.1111/j.1750-2659.2010.00149.x.
Suwannakarn et al., "Typing (A/B) and subtyping (H1/H3/H5) of influenza A viruses by multiplex real-time RT-PCR assays," Journal of Virological Methods, 2008, pp. 25-31, vol. 152, Elsevier B.V., NL.
Wang et al., "Detection of novel (swine origin) H1N1 influenza A virus by quantitative real-time RT-PCR," J Clin Microbiol. Aug. 2009, pp. 2675-2677, vol. 47, No. 8, American Society for Microbiology (ASM), Washington D.C., US. doi:10.1128/JCM.01087-09.
Whiley et al., "Detection of novel influenza A(H1N1) virus by real-time RT-PCR," Journal of Clinical Virology, 2009, pp. 203-204, vol. 45, Elsevier B.V., NL.
Whiley et al., "False-Negative Results in Nucleic Acid Amplification Tests-Do We Need to Routinely Use Two Genetic Targets in all Assays to Overcome Problems Caused by Sequence Variation?," Crit. Rev. Microbiol. 2008, 34:71-76, Informa Healthcare USA.
World Health Organization, "CDC protocol of realtime RTPCR for swine influenza A(H1N1)," revision 1, Center for Disease Control, [report], Apr. 30, 2009, pp. 1-8, Atlanta, US. CDC Ref. #I-007-05.
Written Opinion of the International Searching Authority, International Patent Application No. PCT/US2011/043736, dated Jan. 12, 2013.
Yang et al., "Simultaneous typing and HA/NA subtyping of influenza A and B viruses including the pandemic influenza A/H1N1 2009 by multiplex real-time RT-PCR", Journal of Virological Methods, Jul. 1, 2010, pp. 37-44, vol. 167, No. 1, Elsevier B.V., NL.
Yea et al., "A new RT-PCR assay specific for influenza A(H2), multiplexed with an assay specific for HPAI A(H5N1)," Molecular and Cellular Probes, 2010, pp. 364-369, vol. 24, Elsevier B.V., NL.
Zuckerman et al., "Diagnosis of swine-lineage influenza A (H1N1) virus infection," The Lancet, Jun. 20, 2009, p. 2107, vol. 373, Elsevier B.V., NL.
European Patent Office Examination Report, Application No. 11746688.8, dated May 2, 2014.
EPO Communication pursuant to Article 94(3), European Patent Application No. 11 746 688.8, dated Dec. 18, 2015.

* cited by examiner

SEQUENCE LISTING

```
<160> NUMBER OF SEQ ID NOS: 106

<210> SEQ ID NO 1
<211> LENGTH: 19
<212> TYPE: DNA
<213> ORGANISM: Influenza A virus

<400> SEQUENCE: 1

aagtcgaaac ccaggaaac                                                19


<210> SEQ ID NO 2
<211> LENGTH: 18
<212> TYPE: DNA
<213> ORGANISM: Influenza A virus

<400> SEQUENCE: 2

catgcccact tgctactg                                                 18


<210> SEQ ID NO 3
<211> LENGTH: 22
<212> TYPE: DNA
<213> ORGANISM: Influenza A virus

<400> SEQUENCE: 3

catacacaca agcaggcagg ca                                            22


<210> SEQ ID NO 4
<211> LENGTH: 24
<212> TYPE: DNA
<213> ORGANISM: Influenza A virus

<400> SEQUENCE: 4

aagacctcat tttcctggca cggt                                          24


<210> SEQ ID NO 5
<211> LENGTH: 18
<212> TYPE: DNA
<213> ORGANISM: Influenza A virus

<400> SEQUENCE: 5

cacggtcagc actcattc                                                 18


<210> SEQ ID NO 6
<211> LENGTH: 20
<212> TYPE: DNA
<213> ORGANISM: Influenza A virus

<400> SEQUENCE: 6
```

ttcaaagtca tgcccacttg 20

<210> SEQ ID NO 7
<211> LENGTH: 25
<212> TYPE: DNA
<213> ORGANISM: Influenza A virus

<400> SEQUENCE: 7
atcagttgca cataaatcct gcctg 25

<210> SEQ ID NO 8
<211> LENGTH: 20
<212> TYPE: DNA
<213> ORGANISM: Influenza A virus

<400> SEQUENCE: 8
attggtggaa tcgggagatt 20

<210> SEQ ID NO 9
<211> LENGTH: 23
<212> TYPE: DNA
<213> ORGANISM: Influenza A virus

<400> SEQUENCE: 9
aggtatttat ttcttctctc atc 23

<210> SEQ ID NO 10
<211> LENGTH: 26
<212> TYPE: DNA
<213> ORGANISM: Influenza A virus

<400> SEQUENCE: 10
tccaaatgtg cactgaactc aaactc 26

<210> SEQ ID NO 11
<211> LENGTH: 27
<212> TYPE: DNA
<213> ORGANISM: Influenza A virus

<400> SEQUENCE: 11
tagtcgtcca tcataatcac tgagttt 27

<210> SEQ ID NO 12
<211> LENGTH: 17
<212> TYPE: DNA
<213> ORGANISM: Influenza A virus

<400> SEQUENCE: 12
tggcgtctca aggcacc 17

<210> SEQ ID NO 13
<211> LENGTH: 21
<212> TYPE: DNA
<213> ORGANISM: Influenza A virus

<400> SEQUENCE: 13
ttccaccaat cattcttccg a 21

<210> SEQ ID NO 14
<211> LENGTH: 27
<212> TYPE: DNA
<213> ORGANISM: Influenza A virus

<400> SEQUENCE: 14
atcatatgaa caaatggaga ctggtgg 27

<210> SEQ ID NO 15
<211> LENGTH: 24
<212> TYPE: DNA
<213> ORGANISM: Influenza A virus

<400> SEQUENCE: 15
cgccaggatg ccacagaaat caga 24

<210> SEQ ID NO 16
<211> LENGTH: 25
<212> TYPE: DNA
<213> ORGANISM: Influenza A virus

<400> SEQUENCE: 16
tgctctgatt tctgtggcat cctgg 25

<210> SEQ ID NO 17
<211> LENGTH: 19
<212> TYPE: DNA
<213> ORGANISM: Influenza A virus

<400> SEQUENCE: 17
tagaagagca tcccagtgc 19

<210> SEQ ID NO 18
<211> LENGTH: 18
<212> TYPE: DNA
<213> ORGANISM: Influenza A virus

<400> SEQUENCE: 18
ccattgtttg cttggcgc 18

<210> SEQ ID NO 19
<211> LENGTH: 26
<212> TYPE: DNA
<213> ORGANISM: Influenza A virus

<400> SEQUENCE: 19
aaggacccta agaaaacagg aggacc 26

<210> SEQ ID NO 20
<211> LENGTH: 29
<212> TYPE: DNA
<213> ORGANISM: Influenza A virus

<400> SEQUENCE: 20
ttcttctttg tcataaagga tgagttctc 29

<210> SEQ ID NO 21
<211> LENGTH: 20
<212> TYPE: DNA
<213> ORGANISM: Influenza A virus

<400> SEQUENCE: 21
caacctgaat gatgccacat 20

<210> SEQ ID NO 22
<211> LENGTH: 20
<212> TYPE: DNA
<213> ORGANISM: Influenza A virus

<400> SEQUENCE: 22
tcggtcattg attccacgtt 20

<210> SEQ ID NO 23
<211> LENGTH: 23
<212> TYPE: DNA
<213> ORGANISM: Influenza A virus

<400> SEQUENCE: 23
agagcgcttg ttcgcaccgg aat 23

<210> SEQ ID NO 24
<211> LENGTH: 27
<212> TYPE: DNA
<213> ORGANISM: Influenza A virus

<400> SEQUENCE: 24
cagaatgtgc tctctaatgc aaggttc 27

<210> SEQ ID NO 25
<211> LENGTH: 31
<212> TYPE: DNA
<213> ORGANISM: Influenza A virus

<400> SEQUENCE: 25
tcattctgat taactccatt gctattgttc c 31

<210> SEQ ID NO 26
<211> LENGTH: 19
<212> TYPE: DNA
<213> ORGANISM: Influenza A virus

<400> SEQUENCE: 26
agtggtcagc ctgatgaga 19

<210> SEQ ID NO 27
<211> LENGTH: 22
<212> TYPE: DNA
<213> ORGANISM: Influenza A virus

<400> SEQUENCE: 27
cttaaatctt caaatgcagc ag 22

<210> SEQ ID NO 28
<211> LENGTH: 27
<212> TYPE: DNA
<213> ORGANISM: Influenza A virus

<400> SEQUENCE: 28
caaatgaaaa cccagctcac aagagtc 27

<210> SEQ ID NO 29
<211> LENGTH: 24
<212> TYPE: DNA
<213> ORGANISM: Influenza A virus

<400> SEQUENCE: 29
tggcatgcca tccacaccaa ttga 24

<210> SEQ ID NO 30
<211> LENGTH: 18
<212> TYPE: DNA

<213> ORGANISM: Influenza A virus

<400> SEQUENCE: 30
actgggccat aaggacca 18

<210> SEQ ID NO 31
<211> LENGTH: 18
<212> TYPE: DNA
<213> ORGANISM: Influenza A virus

<400> SEQUENCE: 31
ccgctgaatg ctgccata 18

<210> SEQ ID NO 32
<211> LENGTH: 29
<212> TYPE: DNA
<213> ORGANISM: Influenza A virus

<400> SEQUENCE: 32
agtggaggaa ataccaatca acaaaaggc 29

<210> SEQ ID NO 33
<211> LENGTH: 23
<212> TYPE: DNA
<213> ORGANISM: Influenza A virus

<400> SEQUENCE: 33
cgctgcactg agaatgtagg ctg 23

<210> SEQ ID NO 34
<211> LENGTH: 20
<212> TYPE: DNA
<213> ORGANISM: Influenza A virus

<400> SEQUENCE: 34
gcgaacaatt caacagacac 20

<210> SEQ ID NO 35
<211> LENGTH: 18
<212> TYPE: DNA
<213> ORGANISM: Influenza A virus

<400> SEQUENCE: 35
gatttcccag gatccagc 18

<210> SEQ ID NO 36
<211> LENGTH: 30
<212> TYPE: DNA
<213> ORGANISM: Influenza A virus

<400> SEQUENCE: 36
tagacacagt actagaaaag aatgtaacag 30

<210> SEQ ID NO 37
<211> LENGTH: 23
<212> TYPE: DNA
<213> ORGANISM: Influenza A virus

<400> SEQUENCE: 37
atgcaatggg gctacccctc tta 23

<210> SEQ ID NO 38
<211> LENGTH: 20

<212> TYPE: DNA
<213> ORGANISM: Influenza A virus

<400> SEQUENCE: 38
acgtgttacc caggagattt 20

<210> SEQ ID NO 39
<211> LENGTH: 20
<212> TYPE: DNA
<213> ORGANISM: Influenza A virus

<400> SEQUENCE: 39
cttggggaat atctcaaacc 20

<210> SEQ ID NO 40
<211> LENGTH: 27
<212> TYPE: DNA
<213> ORGANISM: Influenza A virus

<400> SEQUENCE: 40
tcgattatga ggagctaaga gagcaat 27

<210> SEQ ID NO 41
<211> LENGTH: 27
<212> TYPE: DNA
<213> ORGANISM: Influenza A virus

<400> SEQUENCE: 41
attgctctct tagctcctca taatcga 27

<210> SEQ ID NO 42
<211> LENGTH: 18
<212> TYPE: DNA
<213> ORGANISM: Influenza A virus

<400> SEQUENCE: 42
gtaacggcag catgtcct 18

<210> SEQ ID NO 43
<211> LENGTH: 20
<212> TYPE: DNA
<213> ORGANISM: Influenza A virus

<400> SEQUENCE: 43
tagagacttt gttggtcagc 20

<210> SEQ ID NO 44
<211> LENGTH: 23
<212> TYPE: DNA
<213> ORGANISM: Influenza A virus

<400> SEQUENCE: 44
tggtgaatgc cccatagcac gag 23

<210> SEQ ID NO 45
<211> LENGTH: 22
<212> TYPE: DNA
<213> ORGANISM: Influenza A virus

<400> SEQUENCE: 45
agaatgaact attactggac ac 22

<210> SEQ ID NO 46

<211> LENGTH: 20
<212> TYPE: DNA
<213> ORGANISM: Influenza A virus

<400> SEQUENCE: 46
ggactggtgt atctgaaatg 20

<210> SEQ ID NO 47
<211> LENGTH: 26
<212> TYPE: DNA
<213> ORGANISM: Influenza A virus

<400> SEQUENCE: 47
tagagccggg agacaaaata acattc 26

<210> SEQ ID NO 48
<211> LENGTH: 26
<212> TYPE: DNA
<213> ORGANISM: Influenza A virus

<400> SEQUENCE: 48
actggaaatc tagtggtacc gagata 26

<210> SEQ ID NO 49
<211> LENGTH: 27
<212> TYPE: DNA
<213> ORGANISM: Influenza A virus

<400> SEQUENCE: 49
taccagatcc agcatttctt tccattg 27

<210> SEQ ID NO 50
<211> LENGTH: 20
<212> TYPE: DNA
<213> ORGANISM: Influenza A virus

<400> SEQUENCE: 50
agcacaaaat tgagactggc 20

<210> SEQ ID NO 51
<211> LENGTH: 19
<212> TYPE: DNA
<213> ORGANISM: Influenza A virus

<400> SEQUENCE: 51
cctgctcatt ttgatggtg 19

<210> SEQ ID NO 52
<211> LENGTH: 24
<212> TYPE: DNA
<213> ORGANISM: Influenza A virus

<400> SEQUENCE: 52
caggattgag gaatgtcccg tcta 24

<210> SEQ ID NO 53
<211> LENGTH: 23
<212> TYPE: DNA
<213> ORGANISM: Influenza A virus

<400> SEQUENCE: 53
accgtaccat ccatctacca tcc 23

<210> SEQ ID NO 54
<211> LENGTH: 20
<212> TYPE: DNA
<213> ORGANISM: Influenza A virus

<400> SEQUENCE: 54
acagttcaca gcagtaggta 20

<210> SEQ ID NO 55
<211> LENGTH: 22
<212> TYPE: DNA
<213> ORGANISM: Influenza A virus

<400> SEQUENCE: 55
ctggcttctt accttttcat at 22

<210> SEQ ID NO 56
<211> LENGTH: 27
<212> TYPE: DNA
<213> ORGANISM: Influenza A virus

<400> SEQUENCE: 56
ttgatgatgg tttcctggac atttgga 27

<210> SEQ ID NO 57
<211> LENGTH: 29
<212> TYPE: DNA
<213> ORGANISM: Influenza A virus

<400> SEQUENCE: 57
tcttcacatt tgaatcgtgg tagtccaaa 29

<210> SEQ ID NO 58
<211> LENGTH: 28
<212> TYPE: DNA
<213> ORGANISM: Influenza A virus

<400> SEQUENCE: 58
tcattttcca atagaaccaa cagttcgg 28

<210> SEQ ID NO 59
<211> LENGTH: 24
<212> TYPE: DNA
<213> ORGANISM: Influenza A virus

<400> SEQUENCE: 59
gaagcaaaat taaacagaga agaa 24

<210> SEQ ID NO 60
<211> LENGTH: 21
<212> TYPE: DNA
<213> ORGANISM: Influenza A virus

<400> SEQUENCE: 60
tagagcacat ccagaaactg a 21

<210> SEQ ID NO 61
<211> LENGTH: 29
<212> TYPE: DNA
<213> ORGANISM: Influenza A virus

<400> SEQUENCE: 61
atcaacaagg atttaccaga ttttggcga 29

<210> SEQ ID NO 62
<211> LENGTH: 28
<212> TYPE: DNA
<213> ORGANISM: Influenza A virus

<400> SEQUENCE: 62
accaatgaac tggcgacagt tgaataga 28

<210> SEQ ID NO 63
<211> LENGTH: 20
<212> TYPE: DNA
<213> ORGANISM: Influenza A virus

<400> SEQUENCE: 63
aggtttgttt ggagccattg 20

<210> SEQ ID NO 64
<211> LENGTH: 20
<212> TYPE: DNA
<213> ORGANISM: Influenza A virus

<400> SEQUENCE: 64
ttgttgaatt ctttgcccac 20

<210> SEQ ID NO 65
<211> LENGTH: 24
<212> TYPE: DNA
<213> ORGANISM: Influenza A virus

<400> SEQUENCE: 65
tcattgaagg ggggtggact ggaa 24

<210> SEQ ID NO 66
<211> LENGTH: 25
<212> TYPE: DNA
<213> ORGANISM: Influenza A virus

<400> SEQUENCE: 66
tggactggaa tggtagatgg ttggt 25

<210> SEQ ID NO 67
<211> LENGTH: 33
<212> TYPE: DNA
<213> ORGANISM: Influenza A virus

<400> SEQUENCE: 67
tcattttctc aattacagaa ttcaccttgt ttg 33

<210> SEQ ID NO 68
<211> LENGTH: 22
<212> TYPE: DNA
<213> ORGANISM: Influenza A virus

<400> SEQUENCE: 68
atcatacaga aaatgcttat gt 22

<210> SEQ ID NO 69
<211> LENGTH: 18
<212> TYPE: DNA
<213> ORGANISM: Influenza A virus

<400> SEQUENCE: 69
magcagagtc cagtagta 18

<210> SEQ ID NO 70
<211> LENGTH: 29
<212> TYPE: DNA
<213> ORGANISM: Influenza A virus

<400> SEQUENCE: 70
ttcacattat agcagaagat tcaccccag 29

<210> SEQ ID NO 71
<211> LENGTH: 24
<212> TYPE: DNA
<213> ORGANISM: Influenza A virus

<400> SEQUENCE: 71
accccagaaa tagccaaaag accc 24

<210> SEQ ID NO 72
<211> LENGTH: 23
<212> TYPE: DNA
<213> ORGANISM: Influenza A virus

<400> SEQUENCE: 72
ttgaggcaaa tggaaatcta ata 23

<210> SEQ ID NO 73
<211> LENGTH: 21
<212> TYPE: DNA
<213> ORGANISM: Influenza A virus

<400> SEQUENCE: 73
tacattctgg aaaggaagac t 21

<210> SEQ ID NO 74
<211> LENGTH: 27
<212> TYPE: DNA
<213> ORGANISM: Influenza A virus

<400> SEQUENCE: 74
agtagaggct ttggatcagg aatcatc 27

<210> SEQ ID NO 75
<211> LENGTH: 28
<212> TYPE: DNA
<213> ORGANISM: Influenza A virus

<400> SEQUENCE: 75
tgtttatagc tccctgaggt gtttgaca 28

<210> SEQ ID NO 76
<211> LENGTH: 28
<212> TYPE: DNA
<213> ORGANISM: Influenza A virus

<400> SEQUENCE: 76
cattggtgca tttgaggtga tgattcct 28

<210> SEQ ID NO 77
<211> LENGTH: 20
<212> TYPE: DNA
<213> ORGANISM: Influenza A virus

<400> SEQUENCE: 77
actaatgcta ctgagctggt 20

<210> SEQ ID NO 78
<211> LENGTH: 21
<212> TYPE: DNA
<213> ORGANISM: Influenza A virus

<400> SEQUENCE: 78
cttattttgg aagccatcac a 21

<210> SEQ ID NO 79
<211> LENGTH: 27
<212> TYPE: DNA
<213> ORGANISM: Influenza A virus

<400> SEQUENCE: 79
atccttgatg gagaaaactg cacacta 27

<210> SEQ ID NO 80
<211> LENGTH: 27
<212> TYPE: DNA
<213> ORGANISM: Influenza A virus

<400> SEQUENCE: 80
agggtctccc aatagagcat ctattag 27

<210> SEQ ID NO 81
<211> LENGTH: 27
<212> TYPE: DNA
<213> ORGANISM: Influenza A virus

<400> SEQUENCE: 81
tagtgtgcag ttttctccat caaggat 27

<210> SEQ ID NO 82
<211> LENGTH: 22
<212> TYPE: DNA
<213> ORGANISM: Influenza A virus

<400> SEQUENCE: 82
aagactatca ttgctttgag ct 22

<210> SEQ ID NO 83
<211> LENGTH: 20
<212> TYPE: DNA
<213> ORGANISM: Influenza A virus

<400> SEQUENCE: 83
tgaaccagct cagtagcatt 20

<210> SEQ ID NO 84
<211> LENGTH: 31
<212> TYPE: DNA
<213> ORGANISM: Influenza A virus

<400> SEQUENCE: 84
cttcaatttg gtcattcgtg attgttttca c 31

<210> SEQ ID NO 85
<211> LENGTH: 19
<212> TYPE: DNA
<213> ORGANISM: Influenza A virus

<400> SEQUENCE: 85
ctctattggg agaccctca 19

<210> SEQ ID NO 86
<211> LENGTH: 22
<212> TYPE: DNA
<213> ORGANISM: Influenza A virus

<400> SEQUENCE: 86
ctttcattgt taaactccag tg 22

<210> SEQ ID NO 87
<211> LENGTH: 29
<212> TYPE: DNA
<213> ORGANISM: Influenza A virus

<400> SEQUENCE: 87
tgtgatggct tccaaaataa gaaatggga 29

<210> SEQ ID NO 88
<211> LENGTH: 21
<212> TYPE: DNA
<213> ORGANISM: Influenza A virus

<400> SEQUENCE: 88
tgctcaagca tcaggaagaa t 21

<210> SEQ ID NO 89
<211> LENGTH: 20
<212> TYPE: DNA
<213> ORGANISM: Influenza A virus

<400> SEQUENCE: 89
ccctaggagc aattagattc 20

<210> SEQ ID NO 90
<211> LENGTH: 29
<212> TYPE: DNA
<213> ORGANISM: Influenza A virus

<400> SEQUENCE: 90
tctaccaaaa gaagccaaca aactgtaat 29

<210> SEQ ID NO 91
<211> LENGTH: 27
<212> TYPE: DNA
<213> ORGANISM: Influenza A virus

<400> SEQUENCE: 91
tgctgttaat caaaagtatg tctcccg 27

<210> SEQ ID NO 92
<211> LENGTH: 22
<212> TYPE: DNA
<213> ORGANISM: Influenza A virus

<400> SEQUENCE: 92
agctcaataa tgagatcaga tg 22

<210> SEQ ID NO 93
<211> LENGTH: 20
<212> TYPE: DNA
<213> ORGANISM: Influenza A virus

<400> SEQUENCE: 93
ttccctccca accattttct 20

<210> SEQ ID NO 94
<211> LENGTH: 28
<212> TYPE: DNA
<213> ORGANISM: Influenza A virus

<400> SEQUENCE: 94
ccaaatggaa gcattcccaa tgacaaac 28

<210> SEQ ID NO 95
<211> LENGTH: 28
<212> TYPE: DNA
<213> ORGANISM: Influenza A virus

<400> SEQUENCE: 95
caaatatgcc tctagtttgt ttctctgg 28

<210> SEQ ID NO 96
<211> LENGTH: 20
<212> TYPE: DNA
<213> ORGANISM: Influenza A virus

<400> SEQUENCE: 96
tctcaaaagc actcaagcag 20

<210> SEQ ID NO 97
<211> LENGTH: 18
<212> TYPE: DNA
<213> ORGANISM: Influenza A virus

<400> SEQUENCE: 97
ctccgcgttg tatgacca 18

<210> SEQ ID NO 98
<211> LENGTH: 27
<212> TYPE: DNA
<213> ORGANISM: Influenza A virus

<400> SEQUENCE: 98
caaatcaatg ggaagctgaa tagrttg 27

<210> SEQ ID NO 99
<211> LENGTH: 20
<212> TYPE: DNA
<213> ORGANISM: Influenza A virus

<400> SEQUENCE: 99
cctggagaac caacatacaa 20

<210> SEQ ID NO 100
<211> LENGTH: 20
<212> TYPE: DNA
<213> ORGANISM: Influenza A virus

<400> SEQUENCE: 100
caggcattgt cacatttgtg 20

<210> SEQ ID NO 101
<211> LENGTH: 30
<212> TYPE: DNA
<213> ORGANISM: Influenza A virus

<400> SEQUENCE: 101
tgatctaact gactcagaaa tgaacaaact 30

<210> SEQ ID NO 102
<211> LENGTH: 26
<212> TYPE: DNA
<213> ORGANISM: Influenza A virus

<400> SEQUENCE: 102
atcctcagca ttttccctca gttgct 26

<210> SEQ ID NO 103
<211> LENGTH: 1701
<212> TYPE: DNA
<213> ORGANISM: Influenza A virus

<400> SEQUENCE: 103
atgaaggcaa tactagtagt tctgctatat acatttgcaa ccgcaaatgc agacacatta 60
tgtataggtt atcatgcgaa caattcaaca gacactgtag acacagtact agaaaagaat 120
gtaacagtaa cacactctgt taaccttcta gaatacaagc ataacgggaa actatgcaaa 180
ctaagagggg tagccccatt gcatttgggt aaatgtaaca ttgctggctg gatcctggga 240
aatccagagt gtgaatcact ctccacagca agctcatggt cctacattgt ggaaacatct 300
agttcagaca atggaacgtg ttacccagga gatttcatcg attatgagga gctaagagag 360
caattgagct cagtgtcatc atttgaaagg tttgagatat tccccaagac aagttcatgg 420
cccaatcatg actcgaacaa aggtgtaacg gcagcatgtc ctcatgctgg agcaaaaagc 480
ttctacaaaa atttaatatg gctagttaaa aaagaaaatt catacccaaa gctcagcaaa 540
tcctacatta atgataaagg gaaagaagtc ctcgtgctat ggggcattca ccatccatct 600
actagtgctg accaacaaag tctctatcag aatgcagatg catatgtttt tgtggggaca 660
tcaagataca gcaagaagtt caagccggaa atagcaataa gacccaaagt gagggatcaa 720
gaagggagaa tgaactatta ctggacacta gtagagccgg gagacaaaat aacattcgaa 780
gcaactggaa atctagtggt accgagatat gcattcgcaa tggaaagaaa tgctggatct 840
ggtattatca tttcagatac accagtccac gattgcaata caacttgtca gacacccaag 900
ggtgctataa acaccagcct cccatttcag aatatacatc cgatcacaat tggagaatgt 960
ccaaaatatg taaaaagcac aaaattgaga ctggccacag gattgaggaa tgtcccgtct 1020
attcaatcta gaggcctatt tggggccatt gccggtttca ttgaaggggg gtggacaggg 1080
atggtagatg gatggtacgg ttatcaccat caaaatgagc aggggtctgg atatgcagcc 1140
gacctgaaga gcacacagaa tgccattgac gagattacta acaaagtaaa ttctgttatt 1200
gaaaagatga atacacagtt cacagcagta ggtaaagagt tcaaccacct ggaaaaaaga 1260
atagagaatt taaataaaaa ggttgatgat ggtttcctgg acatttggac ttacaattcc 1320
gaactgttgg ttctattgga aaatgaaaga actttggact accacgattc aaatgtgaag 1380
aacttatatg aaaaggtaag aagccagtta aaaaacaatg ccaaggaaat tggaaacggc 1440
tgctttgaat tttaccacaa atgcgataac acgtgcatgg aaagtgtcaa aaatgggact 1500
tatgactacc caaaatactc agaggaagca aaattaaaca gagaagaaat agatggggta 1560
aagctggaat caacaaggat ttaccagatt ttggcgatct attcaactgt cgccagttca 1620
ttggtactgg tagtctccct gggggcaatc agtttctgga tgtgctctaa tgggtctcta 1680
cagtgtagaa tatgtattta a 1701

<210> SEQ ID NO 104
<211> LENGTH: 1577
<212> TYPE: DNA
<213> ORGANISM: Influenza A virus

<400> SEQUENCE: 104
agggtagata atcactcact gagtgacatc gaagccatgg cgtctcaagg caccaaacga 60
tcatatgaac aaatggagac tggtggggag cgccaggatg ccacagaaat cagagcatct 120
gtcggaagaa tgattggtgg aatcgggaga ttctacatcc aaatgtgcac tgaactcaaa 180
ctcagtgatt atgatggacg actaatccag aatagcataa caatagagag gatggtgctt 240
tctgcttttg atgagagaag aaataaatat ctagaagagc atcccagtgc tgggaaggac 300
cctaagaaaa caggaggacc catatataga agaatagacg gaaagtggat gagagaactc 360
atcctttatg acaaagaaga aataaggaga gtttggcgcc aagcaaacaa tggcgaagat 420
gcaacagcag gtcttactca tatcatgatt tggcattcca acctgaatga tgccacatat 480
cagagaacaa gagcgcttgt tcgcaccgga atggatccca gaatgtgctc tctaatgcaa 540
ggttcaacac ttcccagaag gtctggtgcc gcaggtgctg cggtgaaagg agttggaaca 600
atagcaatgg agttaatcag aatgatcaaa cgtggaatca atgaccgaaa tttctggagg 660
ggtgaaaatg gacgaaggac aagggttgct tatgaaagaa tgtgcaatat cctcaaagga 720
aaatttcaaa cagctgccca gagggcaatg atggatcaag taagagaaag tcgaaaccca 780
ggaaacgctg agattgaaga cctcattttc ctggcacggt cagcactcat cctaagggga 840
tcagttgcac ataaatcctg cctgcctgct tgtgtgtatg ggcttgcagt agcaagtggg 900
catgactttg aaagggaagg gtactcactg gtcgggatag acccattcaa attactccaa 960
aacagccaag tggtcagcct gatgagacca aatgaaaacc cagctcacaa gagtcaattg 1020
gtgtggatgg catgccactc tgctgcattt gaagatttaa gagtatcaag tttcataaga 1080
ggaaagaaag tgattccaag aggaaagctt tccacaagag ggtccagat tgcttcaaat 1140 gagaatgtgg aaaccatgga ctccaatacc ctggaactaa gaagcagata ctgggccata 1200
aggaccagga gtggaggaaa taccaatcaa caaaaggcat ccgcaggcca gatcagtgtg 1260
cagcctacat tctcagtgca gcggaatctc ccttttgaaa gagcaactgt tatggcagca 1320
ttcagcggga acaatgaagg acggacatcc gacatgcgaa cagaagttat aagaatgatg 1380
gaaagtgcaa agccagaaga tttgtccttc caggggcggg gagtcttcga gctctcggac 1440
gaaaaggcaa cgaacccgat cgtgccttcc tttgacatga gtaatgaagg gtcttatttc 1500
ttcggagaca atgcagagga gtatgacagt tgaggaaaaa tacccttgtt tctactggtc 1560
atagctgttt tcctgaa 1577

<210> SEQ ID NO 105
<211> LENGTH: 1066
<212> TYPE: DNA
<213> ORGANISM: Influenza A virus

<400> SEQUENCE: 105
gacacaatat gtataggcta ccatgccaac aactcgaccg acactgttga cacagtactt 60
gagaagaatg tgacagtgac acactctgtc aacctacttg aggacagtca caatggaaaa 120
ctatgtctac taaaaggaat agccccacta caattgggta attgcagcgt tgccggatgg 180
atcctaggaa acccagaatg cgaattactg atttccaagg aatcatggtc ctacattgta 240
gagacaccaa atcctgagaa tggaacatgt tacccagggt atttcgccga ctatgaggag 300
ctgagagagc aattgagttc agtatcttca tttgagaggt tcgaaatatt ccccaaagag 360
agctcatggc ccaaccacac cgtaaccgga gtatcagcat catgctccca taacgggaaa 420
agcagttttt acagaaattt gctatggctg acggggaaga atggtttgta tccaaacctg 480
agcaagtcct atgcaaacaa caaagagaaa gaagtccttg tactgtgggg tgttcatcac 540
ccgcctaaca tagggaacca aagggccctc tatcatacag aaaatgctta tgtctctgta 600
gtgtcttcac attatagcag aagattcacc ccagaaatag ccaaaagacc caaggtgaga 660
gatcaggaag gaagaatcaa ctactactgg actctgcttg aacccgggga tacaataata 720
tttgaggcaa atggaaatct aatagcgcca aggtttgctt tcgcactgag tagaggcttt 780
ggatcaggaa tcatcacctc aaatgcacca atggatgaat gtgatgcgaa atgtcaaaca 840
cctcagggag ctataaacag cagtcttcct ttccagaatg tacacccagt cacaatagga 900
gagtgtccaa agtatgtcag gagtgcaaaa ttaagaatgg ttacaggact aaggaacatc 960
ccatccattc aatccagagg tttgtttgga gccattgccg gtttcattga agggggggtgg 1020 actggaatgg tagatggttg gtatggttat caccatcaga atgagc 1066

<210> SEQ ID NO 106
<211> LENGTH: 1701
<212> TYPE: DNA
<213> ORGANISM: Influenza A virus

<400> SEQUENCE: 106
atgaagacta tcattgcttt gagctacatt ttatgtctgg ttttcactca aaaacttccc 60
ggaaatgaca acagcacggc aacgctgtgc ctggggcacc atgcagtgcc aaacggaacg 120
ctagtgaaaa caatcacgaa tgaccaaatt gaagtgacta atgctactga gctggttcag 180
agttcctcaa caggtagaat atgcgacagt cctcaccaaa tccttgatgg agaaaactgc 240
acactaatag atgctctatt gggagaccct cattgtgatg gcttccaaaa taaggaatgg 300
gacctttttg ttgaacgcag caaagcctac agcaactgtt acccttatga tgtgccggat 360
tatgtctccc ttaggtcact agttgcctca tcaggcacgc tggagtttaa caatgaaagc 420
ttcaattgga ctggagtcgc tcagaatgga acaagctctg cttgcaaaag gagatctgat 480
aaaagtttct ttagtagatt gaattggttg caccaattaa aatacaaata tccagcactg 540
aacgtgacta tgccaaacaa tgaaaaattt gacaaattgt acatttgggg ggttcaccac 600
ccgggtacag acagtgacca aatcagccta tatgctcaag catcagggag agtcacagtc 660
tctaccaaaa gaagccaaca aactgtaatc ccgaatatcg gatctagacc ctgggtaagg 720
ggtgtctcca gcagaataag catctattgg acaatagtaa aaccgggaga catacttttg 780
attaacagca cagggaatct aattgctcct cggggttatt tcaaaatacg aagtgggaaa 840
agctcaataa tgaggtcaga tgcacccatt ggcaaatgca attctgaatg catcactcca 900
aatggaagca ttcccaatga caaaccattt caaaatgtaa acaggatcac atatgggccc 960
tgtcccagat atgttaagca aaacactctg aaattggcaa cagggatgcg gaatgtgcca 1020
gagaaacaaa ctagaggcat attcggtgca atcgcgggct tcatagaaaa tggttgggag 1080
ggaatgatgg acggttggta cggtttcagg catcaaaatt ctgagggcac agggcaagca 1140
gcagatctta aaagcactca agcagcaatc aaccaaatca acgggaaact gaataggtta 1200
atcgagaaaa cgaacgagaa attccatcaa attgaaaaag aattctcaga agtagaaggg 1260

-continued

| | |
|---|---|
| agaattcagg acctcgagaa atatgttgag gacactaaaa tagatctctg gtcgtacaat | 1320 |
| gcggagcttc ttgttgccct ggagaaccaa catacaattg atctaactga ctcagaaatg | 1380 |
| aacaaactgt ttgaaagaac aaagaagcaa ctgagggaaa atgctgagga tatgggcaat | 1440 |
| ggttgtttca aaatatacca caaatgtgac aatgcctgca tagggtcaat cagaaatgga | 1500 |
| acttatgacc atgatgtata cagagacgaa gcattgaaca accggttcca gatcaaaggt | 1560 |
| gttgagctga agtcaggata caaagattgg atcctatgga tttcctttgc catatcatgt | 1620 |
| tttttgcttt gtattgtttt gctggggttc atcatgtggg cctgccaaaa aggcaacatt | 1680 |
| aggtgcaaca tttgcatttg a | 1701 |

COMPOSITIONS TO DETECT SEASONAL H1 INFLUENZA A VIRUS NUCLEIC ACIDS

CROSS REFERENCE TO RELATED APPLICATIONS

This application is a divisional application of U.S. patent application Ser. No. 13/809,854, now U.S. Pat. No. 9,234, 249, which is the National Stage Entry of International Application PCT/US2011/043736, filed Jul. 12, 2011, and which claims the benefit under 35 U.S.C. § 119(e) of provisional application No. 61/363,628, filed Jul. 12, 2010, the contents of each are incorporated herein by reference.

FIELD

The present invention is directed to the field of detecting infectious agents, more specifically by using compositions and methods to detect viruses including the swine H1N1 influenza A virus, seasonal H1 influenza A virus and/or seasonal H3 influenza A virus.

BACKGROUND

Influenza viruses (types A, B, and C) are members of the orthomyxoviridae family that cause influenza. Type A influenza viruses infect birds and mammals, including humans, whereas types B and C infect humans only. Influenza viruses are roughly spherical enveloped viruses of about 8-200 nm diameter that contain segmented negative sense genomic RNA. The envelope contains rigid structures that include hemagglutinin (HA) and neuraminidase (NA). Combinations of HA and NA subtypes, which result from genetic reassortment, are used to characterize viral isolates. Generally, influenza viral isolates are identified by nomenclature that includes type, location, isolate number, isolation year, and HA and NA subtypes (e.g., "A/Sydney/7/97(H3N2)" refers to type A, from Sydney, isolate 7, in 1997, with HA 3 and NA 2 subtypes). The common nomenclature for HA and NA uses the first letter of the gene followed by the subtype number (e.g., H#, N# where # is a number). Minor genetic changes that produce antigenic drift may cause influenza epidemics, whereas genetic changes that result in a new HA or NA subtype produce antigenic shift that may cause a pandemic. Analysis of human influenza virus A infections has shown that a few HA and NA combinations are clinically significant in causing pandemics during the 1900s, i.e., H1N1 in 1918, H2N2 in 1957, and H3N2 in 1968.

Influenza viruses that infect birds (e.g., chickens, ducks, pigeons) use combinations of H5, H7 or H9 with any of N1 to N9. Since 1997, avian influenza viruses that have infected humans have included H5N1, H9N2, H7N2, and H7N7 viruses. Even limited human infections caused by an avian influenza virus raise concern for a potential pandemic, resulting in quarantines, and intentional destruction of large numbers of fowl, with accompanying hardship. An avian influenza virus, or variant derived therefrom, that efficiently transfers by human-to-human contact could cause a pandemic (Li et al., 2003, *J. Virol.* 77(12): 6988-6994).

The structure of an influenza virion is generally well understood. In Influenza A, there are generally eight genes, called RNA segments: the HA gene, the NA gene, the NP gene, the M gene, the NS gene, and the genes for the subunits of RNA polymerase, PA, PB1, PB1-F2 and PB2. The HA gene encodes the protein hemagglutinin, which is generally present as a glycoprotein. The NA gene encodes neuraminidase (NA), another glycoprotein. Both are found on the virion surface. The NP gene encodes the nucleoprotein. The nucleoproteins of Influenza A, B, and C are different. The M gene encodes for both the M1 protein and the M2 protein, depending on the reading frame. The M1 protein is the matrix protein, which provides a structure underlying the lipid bilayer. The M2 protein is an ion channel embedded in the lipid bilayer. The NS gene encodes multiple proteins (depending on the reading frame) which are found in the cytosol of an infected cell but not within the virion itself. Each RNA segment consists of RNA joined with several proteins, such as the proteins for RNA polymerase (PB1, PB2, and PA) and NP. Due to the high mutation rate of virus strains, within a given time period and within a given RNA segment, there may be areas of high variation between the sequences found in different sample organisms, and there may be areas which are consistent among the sequences found in different sample organisms.

Due to this variation, Influenza epidemics occur yearly; although both types A and B circulate in the population, type A is usually dominant. These yearly epidemics are partly due to antigenic variation in the HA and NA surface proteins of the virus. In March of 2009, a novel Influenza A virus (2009 H1N1 influenza virus) emerged in North America and globally. (Centers for Disease Control and Prevention. 2009. Swine Influenza A (H1N1) Infection in Two Children—Southern California, March-April 2009. MMWR 58 (Dispatch); 1-3.) The 2009 H1N1 influenza virus is considered a reassortment virus composed of two genes from influenza viruses that normally circulate in swine in Europe and Asia in addition to bird (avian) and human genes. The 2009 H1N1 influenza virus is also considered an Influenza Virus of Swine Origin (SOIV). The symptoms for the 2009 H1N1 virus are similar to those of seasonal influenza strains, however diarrhea and vomiting may be more commonly reported with the 2009 H1N1 virus.

Human influenza viruses produce highly contagious, acute respiratory disease that results in significant morbidity and economic costs, with significant mortality among very young, elderly, and immuno-compromised subpopulations. A typical influenza virus infection in humans has a short incubation period (1 to 2 days) and symptoms that last about a week (e.g., abrupt onset of fever, sore throat, cough, headache, myalgia, malaise and anorexia), which may lead to pneumonia causing increased morbidity and mortality in pediatric, elderly, and immuno-compromised populations. With the 2009 H1N1 virus, young children, pregnant women, and those with underlying health conditions may be at greater risk for severe complications. Optimal protection against infection requires annual inoculation with a vaccine that includes a combination of types A and B of the most likely subtypes for that year, based on global epidemiological surveillance. To be effective in treatment, pharmaceuticals that block viral entry into cells or decrease viral release from infected cells must be administered within 48 hrs of symptoms onset. Such antiviral agents may include oseltamivir (trade name TAMIFLU™), zanamivir (RELENZA™), amantadine and rimantadine, which have been approved for use in the United States for treating influenza. The CDC recommends the use of oseltamivir or zanamivir for patients with the 2009 H1N1 influenza virus as this virus is resistant to amantadine and rimantadine. It is apparent, then, that proper identification of the influenza strain causing an infection is useful in determining the proper course of treatment.

A variety of methods have been used to detect influenza viruses clinically. Viral culture in vitro (in monkey kidney cells) followed by visual analysis and/or hemadsorption using microbiological methods can detect influenza viruses A and B in specimens (e.g., nasopharyngeal or throat swab, nasal or bronchial wash, nasal aspirate, or sputum). Other detection tests include immunofluorescence assays (IFA), enzyme immunoassays (EIA), and enzyme-linked immunosorbent assays (ELISA) that use antibodies specific to influenza virus antigens. Examples include a sandwich microsphere-based IFA that uses influenza A- or B-specific monoclonal antibodies and flow cytometry (Yan et al., 2004, *J. Immunol. Methods* 284(1-2): 27-38), monoclonal antibody-based EIA tests (DIRECTIGEN® FLU A and DIRECTIGEN® FLU A+B, Becton, Dickinson and Co., Franklin Lakes, N.J., and QUICKVUE® Influenza Test, Quidel, San Diego, Calif.), and an immunoassay that produces a color change due to increased thickness of molecular thin films when an immobilized antibody binds an influenza A or B nucleoprotein (FLU OIA®, Biostar Inc., Boulder, Colo.). Another chromagenic assay detects viral NA activity by substrate cleavage (ZSTAT FLU®, ZymeTx, Inc., Oklahoma City, Okla.). Assays are known that rely on reverse-transcriptase polymerase chain reactions (RT-PCR) to amplify influenza viral sequences to detect influenza A and B viruses (e.g., Templeton et al., 2004, *J. Clin. Microbiol.* 42(4):1564-69; Frisbie et al., 2004, *J. Clin. Microbiol.* 42(3):1181-84; Boivin et al., 2004, *J. Clin. Microbiol.,* 42(1):45-51; Habib-Bein et al., 2003, *J. Clin. Microbiol.* 41(8):3597-3601; Li et al., 2001, *J. Clin. Microbiol.* 39(2): 696-704; van Elden et al., 2001, *J. Clin. Microbiol.* 39(1): 196-200; Fouchier et al., 2000, *J. Clin. Microbiol.* 38(11): 4096-101; Ellis et al., 1997, *J. Clin. Microbiol.* 35(8): 2076-2082; PCT Nos. WO 2004 057021, WO 02 00884, WO 00 17391, and WO 97/16570, EP Publ. No. 1 327 691 A2, U.S. Pat. No. 6,015,664, and PROFLU-1™ and HEXAPLEX™ tests, Prodesse, Milwaukee, Wis.). Serology detects seroconversion associated with 2009 H1N1 influenza virus, seasonal H1 influenza A and/or seasonal H3 influenza A virus infections by detecting antibodies present in acute and convalescent sera from patients with influenza symptoms. Detection methods have associated advantages and disadvantages related to sensitivity, specificity, assay and handling time, required equipment, and exposure of technical personnel to infectious agents with related safety requirements for laboratories and personnel. Generally, culture and serological tests require longer completion times (5 days to 2 weeks) with potentially greater exposure of technical personnel to infectious agents. Immunoassays are generally faster (30 min to 4 hrs) but often require substantial sample handling and rely on subjective determination of results by technical personnel. There is a need for a test that provides sensitive, specific detection influenza viruses, including the 2009 H1N1 influenza virus strain, in a relatively short time, with a minimum of exposure of technical personnel to infectious agents, so that diagnosis is completed in sufficient time to permit effective therapeutic treatment of an infected person.

SUMMARY

An embodiment disclosed herein is a composition that includes at least one nucleic acid oligomer specific for swine H1N1 influenza A virus made up of sequences consisting of fragments of the nucleic acid sequence encoding the NP protein or the H1 protein, specific for swine H1N1 influenza A virus or their completely complementary sequences, or DNA equivalents thereof. Particular embodiments include a composition that includes at least one nucleic acid oligomer which targets the swine H1N1 influenza A virus comprising at least 18 contiguous nucleic acids of a sequence encoding the NP protein or a H1 protein which targets the swine H1N1 influenza A virus, or their completely complementary sequences, or DNA equivalents thereof. The nucleic acid oligomer which targets the swine H1N1 influenza A virus comprising at least 18 contiguous nucleic acids of the sequence encoding a NP protein or a H1 protein which targets the swine H1N1 influenza A virus, or its complement, may also have one or more additional nucleic acids at the 5' end and/or may have a total of no more than 50 nucleic acids.

Additional particular embodiments include nucleic acid oligomers in which at least one oligomer is selected from the sequences consisting of (SEQ ID NOS:1, 5, 8, 12, 17, 21, 26 and 30, or SEQ ID NOS:34, 38, 42, 45, 50, 54 and 59), and/or at least one oligomer is selected from the sequences consisting of (SEQ ID NOS:2, 6, 9, 13, 18, 22, 27 and 31, or SEQ ID NOS:35, 39, 43, 46, 51, 55 and 60). Another particular embodiment also includes at least one oligomer selected from sequences consisting of (SEQ ID NOS:3, 4, 7, 10, 11, 14, 15, 16, 19, 20, 23, 24, 25, 28, 29, 32 and 33, or SEQ ID NOS:36, 37, 40, 41, 44, 47, 48, 49, 52, 53, 56, 57, 58, 61 and 62). In a particular embodiment that includes an oligomer selected from sequences consisting of (SEQ ID NOS:3, 4, 7, 10, 11, 14, 15, 16, 19, 20, 23, 24, 25, 28, 29, 32 and 33, SEQ ID NOS: 36, 37, 40, 41, 44, 47, 48, 49, 52, 53, 56, 57, 58, 61 and 62), the oligomer also includes at least one detectable label joined directly or indirectly to the oligomer sequence. A particular label is one that is detectable in a homogeneous assay system. In one aspect, the oligomer is labeled with two labels that are a fluorophore and a quencher. Particular embodiments of these compositions are kits that include at least one of the specified nucleic acid oligomers specific for swine H1N1 influenza A virus. Further embodiments include methods for detectably amplifying one or more of a seasonal H1 influenza A virus, a seasonal H3 influenza A virus or an H1N1 influenza A virus using one or more of these oligomers.

Another embodiment disclosed herein is a composition that includes at least one nucleic acid oligomer specific for seasonal H1 influenza A virus made up of sequences consisting of fragments of the nucleic acid sequence encoding the H1 protein of influenza A, or their completely complementary sequences, or DNA equivalents thereof. The nucleic acid oligomer specific for the seasonal H1 influenza A comprising at least 18 contiguous nucleic acids of the nucleic acid sequence encoding the H1 protein from the seasonal H1 influenza A, or its complement, may also have one or more additional non-influenza sequence nucleic acids at the 5' end and/or may have a total of no more than 50 nucleic acids. Further embodiments include methods for detectably amplifying an influenza A virus using one or more of these oligomers.

Additional particular embodiments include at least one oligomer selected from the sequences consisting of (SEQ ID NOS:63, 68 and 72) and/or at least one oligomer selected from the sequences consisting of (SEQ ID NOS:64, 69 and 73). Another particular embodiment also includes at least one oligomer selected from sequences consisting of (SEQ ID NOS:65, 66, 67, 70, 71, 74, 75 and 76). In a particular embodiment, the oligomer selected from sequences consisting of (SEQ ID NOS: 65, 66, 67, 70, 71, 74, 75 and 76) includes at least one detectable label joined directly or indirectly to the oligomer sequence. Particular embodiments include a label that is detectable in a homogeneous assay system. In one aspect, the oligomer is labeled with two labels that are a fluorophore and a quencher. Particular embodiments of the compositions are kits that include at least one of the specified nucleic acid oligomers specific for seasonal H1 influenza A. Further embodiments include methods for detectably amplifying an influenza A virus using one or more of these oligomers.

Another embodiment disclosed herein is a composition that includes at least one nucleic acid oligomer specific for seasonal H3 influenza A made up of sequences consisting of fragments of the nucleic acid sequence encoding the H3 protein of influenza A, or their completely complementary sequences, or DNA equivalents thereof. The nucleic acid oligomer specific for the seasonal H3 influenza A comprising at least 18 contiguous nucleic acids of the nucleic acid sequence encoding the H1 protein from the seasonal H3 influenza A, or its complement, may also have one or more additional non-influenza sequence nucleic acids at the 5' end and/or may have a total of no more than 50 nucleic acids. Further embodiments include methods for detectably amplifying an influenza A virus using one or more of these oligomers.

A particular embodiment includes at least one oligomer comprising a sequence selected from the sequences consisting of (SEQ ID NOS:77, 82, 85, 88, 92, 96 and 99) and/or at least one oligomer selected from the sequences consisting of (SEQ ID NOS:78, 83, 86, 89, 93, 97 and 100). Another particular embodiment also includes at least one oligomer selected from sequences consisting of (SEQ ID NOS:79, 80, 81, 84, 87, 90, 91, 94, 95, 98, 101 and 102). In a particular embodiment, the oligomer selected from sequences consisting of (SEQ ID NOS:79, 80, 81, 84, 87, 90, 91, 94, 95, 98, 101 and 102) includes at least one detectable label joined directly or indirectly to the oligomer sequence. Particular embodiments include a label that is detectable in a homogeneous assay system. In one aspect, the oligomer is labeled with two labels that are a fluorophore and a quencher. Particular embodiments of the compositions are kits that include at least one of the specified nucleic acid oligomers specific for seasonal H3 influenza A. Further embodiments include methods for detectably amplifying an influenza A virus using one or more of these oligomers.

A further embodiment is a composition or a kit including at least one of the specified nucleic acid oligomers specific for swine H1N1 influenza A virus which also includes at least one of the specified nucleic acid oligomers specific for seasonal H1 influenza A virus and/or at least of the specified nucleic acid oligomers specific for seasonal H3 influenza A virus. In one aspect, the kit includes a primer pair. In one aspect, the kit includes a primer pair for amplifying swine H1N1 influenza A virus, seasonal H1 influenza A virus or seasonal H3 influenza A virus. At least one primer member of the primer pair is selected from Table 1, Table 2 or Table 3, respectively. In one aspect, the kit includes a probe. In one aspect, the kit includes a probe with a target hybridizing sequence selected from Tables 1, 2 or 3. In one aspect, the kit is a multiplex kit and includes at least two primer pairs. In one aspect, the kit is a multiplex kit and includes at least two primer pairs for amplifying two or more of swine H1N1 influenza A virus, seasonal H1 influenza A virus or seasonal H3 influenza A virus. At least one primer member of one of the at least two primer pairs is selected from Tables 1, 2 and/or 3. At least one primer member of two of the at least two primer pairs is selected from Tables 1, 2 and/or 3. At least one primer member of each of the at least two primer pairs is selected from Tables 1, 2, and/or 3. In one aspect, the kit includes at least two probes, each independently having a target hybridizing sequence selected from Tables 1, 2 and/or 3. Further embodiments include methods for detectably amplifying an influenza A virus using one or more of these oligomers.

Another embodiment is a reaction mixture for amplifying swine H1N1 influenza A virus, seasonal H1 influenza A virus and/or seasonal H3 influenza A virus, wherein the reaction mixture includes at least one of the specified nucleic acid oligomers specific for swine H1N1 influenza A virus which also includes at least one of the specified nucleic acid oligomers specific for seasonal H1 influenza A and/or at least of the specified nucleic acid oligomers specific for seasonal H3 influenza A. In one aspect, the reaction mixture includes a primer pair. In one aspect, the reaction mixture includes a primer pair for amplifying swine H1N1 influenza A virus, seasonal H1 influenza A virus or seasonal H3 influenza A virus. At least one primer member of the primer pair is selected from Table 1, Table 2 or Table 3, respectively. In one aspect, the reaction mixture includes a probe. In one aspect, the reaction mixture includes a probe with a target hybridizing sequence selected from Tables 1, 2 and/or 3. In one aspect, the reaction mixture is a multiplex reaction mixture and includes at least two primer pairs. In one aspect, the reaction mixture is a multiplex reaction mixture and includes at least two primer pairs for amplifying two or more of swine H1N1 influenza A virus, seasonal H1 influenza A virus or seasonal H3 influenza A virus. At least one primer member of one of the at least two primer pairs is selected from Tables 1, 2 and/or 3. At least one primer member of two of the at least two primer pairs is selected from Tables 1, 2 and/or 3. At least one primer member of each of the at least two primer pairs is selected from Tables 1, 2, and/or 3. In one aspect, the multiplex reaction mixture includes at least two probes, each having a target hybridizing sequence selected from Tables 1, 2 and/or 3. Further embodiments include methods for detectably amplifying an influenza A virus using one or more of these oligomers.

Another embodiment is a method of detecting nucleic acid of swine H1N1 influenza A virus, seasonal H1 influenza A virus and seasonal H3 influenza A virus in a sample, that includes the steps of amplifying a target sequence in a swine H1N1 influenza A virus nucleic acid, seasonal H1 influenza A virus nucleic acid, and/or seasonal H3 influenza A virus contained in a sample by using a nucleic acid polymerase in vitro to produce an amplified product, wherein the target sequence of swine H1N1 influenza A virus is contained in the swine H1N1 influenza A virus or the complete complement thereof, or RNA equivalents thereof, the target sequence of seasonal H1 influenza A virus is contained in the seasonal influenza A virus sequence, or the complete complement thereof or the RNA equivalents thereof, and the target sequence of seasonal H3 influenza A virus is contained in seasonal Influenza A virus, sequence encoding H3, or the complete complement thereof, or the RNA equivalents thereof, and detecting the amplified product.

A particular embodiment of the method also includes the steps of providing an internal control oligomer, amplifying a target sequence contained in the internal control oligomer, and detecting the amplified product made from the internal control oligomer, thereby indicating that the amplifying and detecting steps of the method are properly performed. In another particular embodiment, the method also isolating an influenza virus nucleic acid from the sample containing the H1N1 Influenza A virus, seasonal H1 Influenza A virus, or seasonal H3 Influenza A virus nucleic acid before the amplifying step.

One embodiment is a method for the detection of an influenza A virus from a sample, comprising the steps of:

contacting an influenza A virus nucleic acid from a sample with a primer composition according to Tables 1, 2 and/or 3; providing conditions for amplifying the nucleic acid by a polymerase chain reaction to generate an amplification product from the nucleic acid; and detecting the presence or absence of amplification product, wherein the presence of the amplification product indicates that the sample contained an influenza A virus. In one aspect, the detecting step is a real-time detecting step. In one aspect, the detecting step is a taqman PCR detecting step. In one aspect, the e sample contains an influenza A virus nucleic acid selected from the group consisting of: a H1N1 influenza A virus nucleic acid, a seasonal H1 influenza A virus nucleic acid, a seasonal H3 influenza A virus, and a combination thereof. In one aspect, the sample contains an influenza A virus nucleic acid that is substantially identical to an influenza A virus selected from the group consisting of: a H1N1 influenza A virus nucleic acid, a seasonal H1 influenza A virus nucleic acid and a seasonal H3 influenza A virus, and an amplification product is generated therefrom. In one aspect, the sample contains an influenza A virus nucleic acid that is at least 90% identical to an influenza A virus selected from the group consisting of: a H1N1 influenza A virus nucleic acid, a seasonal H1 influenza A virus nucleic acid and a seasonal H3 influenza A virus, and an amplification product is generated therefrom. In one aspect, the sample contains an influenza A virus nucleic acid that has an H1 gene that is substantially identical to the H1 gene of an influenza A virus selected from the group consisting of: a H1N1 influenza A virus nucleic acid and a seasonal H1 influenza A virus nucleic acid, and an amplification product is generated therefrom. In one aspect, the sample contains an influenza A virus nucleic acid that has an H1 gene that is at least 90% identical to the H1 gene of an influenza A virus selected from the group consisting of: a H1N1 influenza A virus nucleic acid and a seasonal H1 influenza A virus nucleic acid, and an amplification product is generated therefrom. In one aspect, the amplifying step is a multiplex amplification reaction for detecting two or more of an influenza A virus nucleic acid, each of which are independently at least 90% identical to an influenza A virus selected from the group consisting of: a H1N1 influenza A virus nucleic acid, a seasonal H1 influenza A virus nucleic acid and a seasonal H3 influenza A virus.

One embodiment is a method for the detection of an influenza A virus from a sample, comprising the steps of: contacting an influenza A virus nucleic acid from a sample with a composition according to one of Mixture 1 to Mixture 21; providing conditions for amplifying the nucleic acid by a polymerase chain reaction to generate an amplification product from the nucleic acid; and detecting the presence or absence of amplification product, wherein the presence of the amplification product indicates that the sample contained an influenza A virus. In one aspect, the detecting step is a real-time detecting step. In one aspect, the detecting step is a taqman PCR detecting step. In one aspect, the sample contains an influenza A virus nucleic acid selected from the group consisting of: a H1N1 influenza A virus nucleic acid, a seasonal H1 influenza A virus nucleic acid, a seasonal H3 influenza A virus, and a combination thereof, and an amplification product is generated therefrom. In one aspect, the sample contains an influenza A virus nucleic acid that is substantially identical to an influenza A virus selected from the group consisting of: a H1N1 influenza A virus nucleic acid, a seasonal H1 influenza A virus nucleic acid and a seasonal H3 influenza A virus, and an amplification product is generated therefrom. In one aspect, the sample contains an influenza A virus nucleic acid that is at least 90% identical to an influenza A virus selected from the group consisting of: a H1N1 influenza A virus nucleic acid, a seasonal H1 influenza A virus nucleic acid and a seasonal H3 influenza A virus, and an amplification product is generated therefrom. In one aspect, the sample contains an influenza A virus nucleic acid that has an H1 gene that is substantially identical to the H1 gene of an influenza A virus selected from the group consisting of: a H1N1 influenza A virus nucleic acid and a seasonal H1 influenza A virus nucleic acid, and an amplification product is generated therefrom. In one aspect, the sample contains an influenza A virus nucleic acid that has an H1 gene that is at least 90% identical to the H1 gene of an influenza A virus selected from the group consisting of: a H1N1 influenza A virus nucleic acid and a seasonal H1 influenza A virus nucleic acid, and an amplification product is generated therefrom. in one aspect, the amplifying step is a multiplex amplification reaction for detecting two or more of an influenza A virus nucleic acid, each of which are independently at least 90% identical to an influenza A virus selected from the group consisting of: a H1N1 influenza A virus nucleic acid, a seasonal H1 influenza A virus nucleic acid and a seasonal H3 influenza A virus, and an amplification product is generated therefrom.

One embodiment is a method for the detection of an H1N1 Influenza A Virus from a sample, comprising the steps of: contacting an H1N1 Influenza A Virus from a sample with primer pair selected from Table 1; providing conditions for amplifying the nucleic acid by a polymerase chain reaction to generate an amplification product from the nucleic acid; and detecting the presence or absence of amplification product, wherein the presence of the amplification product indicates that the sample contained an H1N1 Influenza A Virus. In one aspect, the detecting step is a real-time detecting step. in one aspect, the detecting step is a taqman PCR detecting step. In one aspect, the detecting step uses a probe selected from Table 1. In one aspect, the sample further contains an influenza A virus nucleic acid selected from the group consisting of: a seasonal H1 influenza A virus nucleic acid, a seasonal H3 influenza A virus, and a combination thereof, and an amplification product is generated therefrom. In one aspect, the amplifying step is a multiplex amplification reaction that further comprises a primer pair from Table 2, a primer pair from Table 3 or a primer pair from Table 2 and a primer pair from Table 3. In one aspect, the detecting step further comprises a probe from Table 2, a probe from Table 3 or a probe from Table 2 and a probe from Table 3. In one aspect, the amplifying step generates a detectable amplification product from an influenza A virus nucleic acid that is at least 90% identical to an influenza A virus nucleic acid selected from the group consisting of: an H1N1 influenza virus nucleic acid, a seasonal H1 influenza A virus nucleic acid, a seasonal H3 influenza A virus, and a combination thereof. in one aspect, the amplification product is detected using a taqman probe having a nucleic acid sequence according to a probe sequence in Table 2 or Table 3.

One embodiment is a method for the detection of a seasonal H1 Influenza A Virus from a sample, comprising the steps of: contacting a seasonal H1 Influenza A Virus nucleic acid from a sample with primer pair selected from Table 2; providing conditions for amplifying the nucleic acid by a polymerase chain reaction to generate an amplification product from the nucleic acid; and detecting the presence or absence of amplification product, wherein the presence of the amplification product indicates that the sample contained a seasonal H1 Influenza A Virus. In one aspect, the detecting step is a real-time detecting step. In one aspect, the detecting step is a taqman PCR detecting step. in one aspect, the detecting step uses a probe selected from Table 2. In one aspect, the sample further contains an influenza A virus nucleic acid selected from the group consisting of: a H1N1 influenza A virus nucleic acid, a seasonal H3 influenza A virus, and a combination thereof, and an amplification product is generated therefrom. In one aspect, the amplifying step is a multiplex amplification reaction that further comprises a primer pair from Table 1, a primer pair from Table 3 or a primer pair from Table 1 and a primer pair from Table 3. in one aspect, the detecting step further comprises a probe from Table 1, a probe from Table 3 or a probe from Table 1 and a probe from Table 3. in one aspect, the amplifying step generates a detectable amplification product from an influenza A virus nucleic acid that is at least 90% identical to an influenza A virus nucleic acid selected from the group consisting of: a H1N1 influenza A virus nucleic acid, a seasonal H3 influenza A virus, and a combination thereof.

One embodiment is a method for the detection of a seasonal H3 Influenza A Virus from a sample, comprising the steps of: contacting a seasonal H3 Influenza A Virus nucleic acid from a sample with primer pair selected from Table 3; providing conditions for amplifying the nucleic acid by a polymerase chain reaction to generate an amplification product from the nucleic acid; and detecting the presence or absence of amplification product, wherein the presence of the amplification product indicates that the sample contained a seasonal H3 Influenza A Virus. In one aspect the detecting step is a real-time detecting step. in one aspect, the detecting step is a taqman PCR detecting step. In one aspect, the detecting step uses a probe selected from Table 3. In one aspect, the sample further contains an influenza A virus nucleic acid selected from the group consisting of: a H1N1 influenza A virus nucleic acid, a seasonal H1 influenza A virus, and a combination thereof, and an amplification product is generated therefrom. In one aspect, the amplifying step is a multiplex amplification reaction that further comprises a primer pair from Table 1, a primer pair from Table 2 or a primer pair from Table 1 and a primer pair from Table 2. In one aspect, the detecting step further comprises a probe from Table 1, a probe from Table 2 or a probe from Table 1 and a probe from Table 2. In one aspect, the amplifying step generates a detectable amplification product from an influenza A virus nucleic acid that is at least 90% identical to an influenza A virus nucleic acid selected from the group consisting of: a H1N1 influenza A virus nucleic acid, a seasonal H1 influenza A virus, a seasonal H3 influenza A virus, and a combination thereof.

One embodiment of the methods further provides a separating step wherein nucleic acids are removed from one or more other components in the sample. in one aspect, the separating step takes place before the amplifying step. In one aspect, the separating step is performed using a target capture oligomer having a tail selected from the group consisting of $dT_{0-3}dA_{12-30}$, and using a solid support having an immobilized probe that is substantially complementary to the tail. In one aspect, the separating step is a non-specific separating step. In one aspect, the non-specific separating step is performed by adhering nucleic acids reversibly to a solid support, followed by washing and elution of the adhered nucleic acids into a substantially aqueous solution (e.g., using a MagNA Pure LC System (Roche) and the MagNA Pure Total Nucleic Acid Isolation Kit (Roche) or a NucliSENS easy MAG System (bioMériuex and the Automated Magnetic Extraction Reagents (bioMérieux), or using a non-specific target capture probe (WO 2008/016988) or comparable nucleic acid extraction instrument(s) and/or reagent kit(s))

DETAILED DESCRIPTION

In one aspect, the present invention involves performing an amplification reaction. Preferably, the amplification reaction is a PCR reaction. However, there are other suitable amplification techniques such as CPR (Cycling Probe Reaction), bDNA (Branched DNA Amplification), SSR (Self-Sustained Sequence Replication), SDA (Strand Displacement Amplification), QBR (Q-Beta Replicase), Re-AMP (Formerly RAMP), NASBA (Nucleic Acid Sequence Based Amplification), RCR (Repair Chain Reaction), LCR (Ligase Chain Reaction), TAS (Transorbtion Based Amplification System), HCS (amplified ribosomal RNA), and TMA (Transcription Mediated Amplification).

The disclosed nucleic acid sequences and methods are useful for amplifying and detecting swine H1N1 influenza A virus, seasonal H1 influenza A virus, and/or seasonal H3 influenza A virus nucleic acids from viral particles present in a sample in a relatively short time so that diagnosis can be made during early stages of infection (e.g., within 48 hr of symptoms) and effective treatment can be initiated. The methods are useful for screening for individuals who have influenza virus infections but who do not exhibit definitive symptoms, particularly for screening patients who have a higher risk of death or serious complications from influenza virus infections, e.g., young, elderly, or immuno-compromised individuals. The methods are further useful for identifying influenza type that is causing an infection so that a proper course of treatment can be applied. The methods are also useful for rapid screening of many samples, such as during an epidemic or pandemic, so that appropriate public health responses can be initiated. The methods are useful because they minimize the risk of exposure of laboratory personnel to infectious agents, such as an avian influenza virus related to swine H1N1 influenza A virus, seasonal H1 influenza A virus, and/or seasonal H3 influenza A virus that have become infectious to humans. Thus, the methods and compositions disclosed herein respond to a need for rapid, sensitive, and specific testing of clinical samples that may contain swine H1N1 influenza A virus, seasonal H1 influenza A virus, and/or seasonal H3 influenza A virus.

Definitions

Seasonal H1 Influenza A includes various strains of Influenza A which have the H1 subtype. Sequences specific for the seasonal H1 Influenza A may be identical to a portion of a single strain or may be a consensus sequence shared between multiple strains. However, to ensure that multiple strains of the seasonal H1 Influenza A virus are detected using the claimed compositions, kits, and methods, the sequences used as primers and probes were designed from regions of the genome that are generally conserved among many strains of seasonal H1 Influenza A virus.

Seasonal H3 Influenza A virus includes various strains of Influenza A which have the H3 subtype. To ensure that multiple strains of the seasonal H3 Influenza A virus are detected using the claimed compositions, kits, and methods, the sequences specific for H3 influenza A virus that were used as primers and probes were designed for regions of the genome that are generally conserved among many strains of seasonal H3 Influenza A virus.

The swine H1N1 influenza A virus, when referred to as such, is a reassortment virus composed of at least two genes from one or more influenza viruses that normally circulate in swine in Europe and Asia, in addition to bird (avian) and human genes. The 2009 swine H1N1 influenza A virus is also considered a swine H1N1 influenza A virus. Sequences specific for the swine H1N1 influenza A virus may represent a consensus sequence between multiple strains or occurrences. To ensure that multiple strains of the swine H1N1 influenza A virus are detected using the claimed and/or disclosed compositions, kits, reaction mixtures and methods, the sequences used as primers and probes were designed from regions of the genome that are conserved among many strains of the swine H1N1 influenza A virus, but that are not conserved in the seasonal H1 influenza A or seasonal H3 influenza A viral sequences.

A "sample" or "specimen", including "biological" or "clinical" samples, refers to a tissue or material derived from a living or dead human or animal which may contain an influenza virus target nucleic acid, including, for example, nasopharyngeal or throat swabs, nasal or bronchial washes, nasal aspirates, sputum, other respiratory tissue or exudates, biopsy tissue including lymph nodes, or body fluids such as blood or urine. A sample may be treated to physically or mechanically disrupt tissue or cell structure to release intracellular nucleic acids into a solution which may contain enzymes, buffers, salts, detergents and the like, to prepare the sample for analysis.

"Nucleic acid" refers to a multimeric compound comprising nucleosides or nucleoside analogs which have nitrogenous heterocyclic bases or base analogs linked together to form a polynucleotide, including conventional RNA, DNA, mixed RNA-DNA, and polymers that are analogs thereof. A nucleic acid "backbone" may be made up of a variety of linkages, including one or more of sugar-phosphodiester linkages, peptide-nucleic acid bonds ("peptide nucleic acids" or PNA; PCT No. WO 95/32305), phosphorothioate linkages, methylphosphonate linkages, or combinations thereof. Sugar moieties of a nucleic acid may be ribose, deoxyribose, or similar compounds with substitutions, e.g., 2' methoxy or 2' halide substitutions. Nitrogenous bases may be conventional bases (A, G, C, T, U), analogs thereof (e.g., inosine or others; see *The Biochemistry of the Nucleic Acids* 5-36, Adams et al., ed., $11^{th}$ ed., 1992), derivatives of purines or pyrimidines (e.g., $N^4$-methyl deoxygaunosine, deaza- or aza-purines, deaza- or aza-pyrimidines, pyrimidine bases with substituent groups at the 5 or 6 position, purine bases with a substituent at the 2, 6 or 8 positions, 2-amino-6-methylaminopurine, $O^6$-methylguanine, 4-thio-pyrimidines, 4-amino-pyrimidines, 4-dimethylhydrazine-pyrimidines, and $O^4$-alkyl-pyrimidines; U.S. Pat. No. 5,378,825 and PCT No. WO 93/13121). Nucleic acids may include one or more "abasic" residues where the backbone includes no nitrogenous base for position(s) of the polymer (U.S. Pat. No. 5,585,481). A nucleic acid may comprise only conventional RNA or DNA sugars, bases and linkages, or may include both conventional components and substitutions (e.g., conventional bases with 2' methoxy linkages, or polymers containing both conventional bases and one or more base analogs). Nucleic acid includes "locked nucleic acid" (LNA), an analogue containing one or more LNA nucleotide monomers with a bicyclic furanose unit locked in an RNA mimicking sugar conformation, which enhance hybridization affinity toward complementary RNA and DNA sequences (Vester and Wengel, 2004, *Biochemistry* 43(42): 13233-41). Embodiments of oligomers that may affect stability of a hybridization complex include PNA oligomers, oligomers that include 2'-methoxy or 2'-fluoro substituted RNA, or oligomers that affect the overall charge, charge density, or steric associations of a hybridization complex, including oligomers that contain charged linkages (e.g., phosphorothioates) or neutral groups (e.g., methylphosphonates).

By "RNA and DNA equivalents" is meant RNA and DNA molecules having essentially the same complementary base pair hybridization properties. RNA and DNA equivalents have different sugar moieties (i.e., ribose versus deoxyribose) and may differ by the presence of uracil in RNA and thymine in DNA. The differences between RNA and DNA equivalents do not contribute to differences in homology because the equivalents have the same degree of complementarity to a particular sequence.

An "oligomer" or "oligonucleotide" refers to a nucleic acid of generally less than 1,000 nucleotides (nt), including those in a size range having a lower limit of about 2 to 5 nt and an upper limit of about 500 to 900 nt. Some particular embodiments are oligomers in a size range with a lower limit of about 5 to 15, 16, 17, 18, 19, or 20 nt and an upper limit of about 50 to 600 nt, and other particular embodiments are in a size range with a lower limit of about 10 to 20 nt and an upper limit of about 22 to 100 nt. Oligomers may be purified from naturally occurring sources, but preferably are synthesized by using any well known enzymatic or chemical method. Oligomers may be referred to by a functional name (e.g., capture probe, primer or promoter primer) but those skilled in the art will understand that such terms refer to oligomers.

By "antisense," "opposite sense," or "negative sense" is meant a nucleic acid molecule completely complementary to a reference, or sense, nucleic acid molecule.

By "sense," "same-sense" or "positive sense" is meant a nucleic acid molecule perfectly homologous to a reference nucleic acid molecule.

By "amplicon" or "amplification product" is meant a nucleic acid molecule generated in a nucleic acid amplification reaction and which is derived from a target nucleic acid. An amplicon or amplification product contains a target nucleic acid sequence that may be of the same or opposite sense as the target nucleic acid.

An "immobilized probe", "immobilized oligomer" or "immobilized nucleic acid" refers to a nucleic acid binding partner that joins a capture oligomer to a support, directly or indirectly. An immobilized probe joined to a support facilitates separation of a capture probe bound target from unbound material in a sample. The immobilized probe hybridizes with the immobilized probe binding region of the capture probe, thereby forming an immobilized probe:capture probe complex. In the presence of a target nucleic acid, an immobilized probe:capture probe:target nucleic acid complex forms. Any support may be used, e.g., matrices or particles free in solution, which may be made of any of a variety of materials, e.g., nylon, nitrocellulose, glass, polyacrylate, mixed polymers, polystyrene, silane polypropylene, or metal. Target capture reagents may optionally include imidazoleum compounds, urea and the like (e.g., WO 2006/121888). Particular embodiments use a support that is magnetically attractable particles, e.g., monodisperse paramagnetic beads (uniform size±5%) to which an immobilized probe is joined directly (e.g., via covalent linkage, chelation, or ionic interaction) or indirectly (e.g., via a linker), where the joining is stable during nucleic acid hybridization conditions.

"Capture-probe," "target capture probe" or "target capture oligomer" refers to a nucleic acid oligomer that is used to separate nucleic acids in a sample from other components of the sample. Typically, the target capture oligomer has at least two regions: the target-hybridizing region; and the binding-pair region, usually on the same oligomer, although the two regions may be present on two different oligomers joined together by one or more linkers. The binding-pair region is sometimes referred to as a tail portion of the capture probe. The target-hybridizing region is a contiguous nucleic acid sequence that is configured to hybridize to nucleic acids in the sample. The target-hybridizing region can be configured to specifically hybridize to a particular nucleic acid species in a group of nucleic acids. In this instance, the target-hybridizing region is configured to be substantially complementary to a given sequence on a particular nucleic acid species. The target-hybridizing region can be configured to specifically hybridize to a subset of nucleic acid species in a group of nucleic acids, wherein the subset share a similar nucleic acid sequence at at least part of their overall sequences. In this instance, the target-hybridizing region is configured to be substantially complementary to this shared similar sequence on these subset of nucleic acid species. The target-hybridizing region can also be configured to non-specifically hybridize to nucleic acids in a group of nucleic acids (WO 2008/016988). In this instance, the target-hybridizing region is not configured to be substantially complementary to any given sequence on a particular nucleic acid species. Rather, the target-hybridizing sequence can be configured to generally hybridize with nucleic acids in a group. Non-specific target capture is designed to separate nucleic acids in a sample from the non-nucleic acid components, whereas specific target capture is designed to separate a particular species or subset of nucleic acids from other nucleic acids and non-nucleic acids in a sample. The binding pair portion of the target capture oligomer is configured to join with a complementary binding pair; typically present on a solid support. When the binding pair portion of the target capture oligomer is itself a nucleic acid sequence, then the complementary binding pair on a solid support is a nucleic acid with a substantially complementary nucleic acid sequence (also referred to as an immobilized probe). Commonly, the binding pair portion of a target capture oligomer is a substantially homopolymeric nucleic acid sequence (e.g., a poly dT and/or a poly dA nucleic acid sequence). In this instance, then, the immobilized probe is a substantially complementary nucleic acid. One common example is a target capture oligomer having a binding pair region that is a $dT_{0\text{-}3}dA_{12\text{-}30}$ nucleic acid sequence. In this instance, the immobilized probe would then be a substantially complementary nucleic acid sequence (e.g., $dA_{0\text{-}3}dT_{12\text{-}30}$). Additionally, a nucleic acid binding-pair region of a capture probe is often made so to not bind nucleic acids in the sample by, for example, giving the nucleic acids a left-handed chirality. In this instance, the immobilized probe is also made left-handed. Thus, the binding pair region and the immobilized probe do not bind nucleic acids in the sample because of the opposite chirality. Other examples of binding pair regions/complementary binding pairs that can be used include; (a) a receptor and ligand pair, (b) an enzyme and substrate pair, (c) an enzyme and cofactor pair, (d) an enzyme and coenzyme pair, (e) an antibody and antigen pair, (f) an antibody fragment and antigen pair, (g) a sugar and lectin pair, (h) a ligand and chelating agent pair, (i) biotin and avidin, (j) biotin and streptavidin, and (k) nickel and histidine.

"Separating" or "purifying" refers to removing one or more components of a sample from one or more other sample components, e.g., removing some nucleic acids from a generally aqueous solution that may also contain proteins, carbohydrates, lipids, or other nucleic acids. In particular embodiments, a separating or purifying step removes the target nucleic acid from at least about 70%, more preferably at least about 90% and, even more preferably, at least about 95% of the other sample components.

An "amplification oligonucleotide" or "amplification oligomer" refers to an oligonucleotide that hybridizes to a target nucleic acid, or its complement, and participates in a nucleic acid amplification reaction, e.g., serving as a primer or and promoter-primer. Particular amplification oligomers contain at least about 10 contiguous bases, and more preferably at least 11, 12, 13, 14, 15, 16, 17, 18, 19, or 20 contiguous bases, that are complementary to a region of the target nucleic acid sequence or its complementary strand. The contiguous bases are preferably at least about 80%, more preferably at least about 90%, and most preferably completely complementary to the target sequence to which the amplification oligomer binds. One skilled in the art will understand that the recited ranges include all whole and rational numbers within the range (e.g., 92% or 98.377%). Particular amplification oligomers are about 10 to about 60 bases long and optionally may include modified nucleotides.

A "primer" refers to an oligomer that hybridizes to a template nucleic acid and has a 3' end that is extended by polymerization. A primer may be optionally modified, e.g., by including a 5' region that is non-complementary to the target sequence. Such modification can include functional additions, such as tags, promoters or other sequences used or useful for manipulating or amplifying the primer or target oligonucleotide.

Within the context of transcription mediated amplification, a primer modified with a 5' promoter sequence may be referred to as a "promoter-primer." A person of ordinary skill in the art of molecular biology or biochemistry will understand that an oligomer that can function as a primer can be modified to include a 5' promoter sequence and then function as a promoter-primer, and, similarly, any promoter-primer can serve as a primer with or without its 5' promoter sequence.

"Nucleic acid amplification" refers to any well known in vitro procedure that produces multiple copies of a target nucleic acid sequence, or its complementary sequence, or fragments thereof (i.e., an amplified sequence containing less than the complete target nucleic acid). Examples of well known nucleic acid amplification procedures include transcription associated methods, such as transcription-mediated amplification (TMA), nucleic acid sequence-based amplification (NASBA) and others (e.g., U.S. Pat. Nos. 5,399,491, 5,554,516, 5,437,990, 5,130,238, 4,868,105, and 5,124,246), replicase-mediated amplification (e.g., U.S. Pat. No. 4,786,600), the polymerase chain reaction (PCR) (e.g., U.S. Pat. Nos. 4,683,195, 4,683,202, and 4,800,159), ligase chain reaction (LCR) (e.g., EP Pat. App. 0320308) and strand-displacement amplification (SDA) (e.g., U.S. Pat. No. 5,422,252). Replicase-mediated amplification uses self-replicating RNA molecules, and a replicase such as QB-replicase. PCR amplification uses DNA polymerase, primers, and thermal cycling steps to synthesize multiple copies of the two complementary strands of DNA or cDNA. LCR amplification uses at least four separate oligonucleotides to amplify a target and its complementary strand by using multiple cycles of hybridization, ligation, and denaturation. SDA uses a primer that contains a recognition site for a restriction endonuclease that will nick one strand of a hemimodified DNA duplex that includes the target sequence, followed by amplification in a series of primer extension and strand displacement steps. Particular embodiments use PCR or TMA, but it will be apparent to persons of ordinary skill in the art that oligomers disclosed herein may be readily used as primers in other amplification methods.

Transcription associated amplification uses a DNA polymerase, an RNA polymerase, deoxyribonucleoside triphosphates, ribonucleoside triphosphates, a promoter-containing oligonucleotide, and optionally may include other oligonucleotides, to ultimately produce multiple RNA transcripts from a nucleic acid template (described in detail in U.S. Pat. Nos. 5,399,491 and 5,554,516, Kacian et al., U.S. Pat. No. 5,437,990, Burg et al., PCT Nos. WO 88/01302 and WO 88/10315, Gingeras et al., U.S. Pat. No. 5,130,238, Malek et al., U.S. Pat. Nos. 4,868,105 and 5,124,246, Urdea et al., PCT No. WO 94/03472, McDonough et al., PCT No. WO 95/03430, and Ryder et al.). Methods that use TMA are described in detail previously (U.S. Pat. Nos. 5,399,491 and 5,554,516).

In methods that detect amplification products in real-time, the term "Threshold cycle" (Ct) is a measure of the emergence time of a signal associated with amplification of target, and is generally 10× standard deviation of the normalized reporter signal. Once an amplification reaches the "threshold cycle", generally there is considered to be a positive amplification product of a sequence to which the probe binds. The identity of the amplification product can then be determined through methods known to one of skill in the art, such as gel electrophoresis, nucleic acid sequencing, and other such well known methods.

As used herein, the term "relative fluorescence unit" ("RFU") is a unit of measurement of fluorescence intensity. RFU varies with the characteristics of the detection means used for the measurement, and can be used as a measurement to compare relative intensities between samples and controls. The analytical sensitivity (limit of detection or LoD) is determined from the median tissue culture infective dose ($TCID_{50}$/ml). The $TCID_{50}$/ml is that amount of a pathogenic agent that will produce pathological change in 50% of cell cultures inoculated.

"Detection probe" refers to a nucleic acid oligomer that hybridizes specifically to a target sequence, including an amplified sequence, under conditions that promote nucleic acid hybridization, for detection of the target nucleic acid. Detection may either be direct (i.e., probe hybridized directly to the target) or indirect (i.e., a probe hybridized to an intermediate structure that links the probe to the target). A probe's target sequence generally refers to the specific sequence within a larger sequence which the probe hybridizes specifically. A detection probe may include target-specific sequences and a non-target-complementary sequence. Such non-target-complementary sequences can include sequences which will confer a desired secondary or tertiary structure, such as a hairpin structure, which can be used to facilitate detection and/or amplification. (e.g., U.S. Pat. Nos. 5,118,801, 5,312,728, 6,835,542, and 6,849,412). Probes of a defined sequence may be produced by techniques known to those of ordinary skill in the art, such as by chemical synthesis, and by in vitro or in vivo expression from recombinant nucleic acid molecules.

By "hybridization" or "hybridize" is meant the ability of two completely or partially complementary nucleic acid strands to come together under specified hybridization assay conditions in a parallel or preferably antiparallel orientation to form a stable structure having a double-stranded region. The two constituent strands of this double-stranded structure, sometimes called a hybrid, are held together by hydrogen bonds. Although these hydrogen bonds most commonly form between nucleotides containing the bases adenine and thymine or uracil (A and T or U) or cytosine and guanine (C and G) on single nucleic acid strands, base pairing can also form between bases which are not members of these "canonical" pairs. Non-canonical base pairing is well-known in the art. (See, e.g., R. L. P. Adams et al., *The Biochemistry of the Nucleic Acids* (11.sup.th ed. 1992).)

By "preferentially hybridize" is meant that under stringent hybridization conditions, an amplification or detection probe oligomer can hybridize to its target nucleic acid to form stable oligomer:target hybrid, but not form a sufficient number of stable oligomer:non-target hybrids. Amplification and detection oligomers that preferentially hybridize to a target nucleic acid are useful to amplify and detect target nucleic acids, but not non-targeted organisms, especially phylogenetically closely related organisms. Thus, the oligomer hybridizes to target nucleic acid to a sufficiently greater extent than to non-target nucleic acid to enable one having ordinary skill in the art to accurately amplify and/or detect the presence (or absence) of nucleic acid derived from the specified influenza viruses as appropriate. In general, reducing the degree of complementarity between an oligonucleotide sequence and its target sequence will decrease the degree or rate of hybridization of the oligonucleotide to its target region. However, the inclusion of one or more non-complementary nucleosides or nucleobases may facilitate the ability of an oligonucleotide to discriminate against non-target organisms.

Preferential hybridization can be measured using techniques known in the art and described herein, such as in the examples provided below. Preferably, there is at least a 10-fold difference between target and non-target hybridization signals in a test sample, more preferably at least a 100-fold difference, and most preferably at least a 1,000-fold difference. Preferably, non-target hybridization signals in a test sample are no more than the background signal level.

By "stringent hybridization conditions," or "stringent conditions" is meant conditions permitting an oligomer to preferentially hybridize to a target nucleic acid (preferably an HA, NA or NP gene or transcript therefrom derived from one or more virus strains of the specified influenza A virus types) and not to nucleic acid derived from a closely related non-target nucleic acids. Stringent hybridization conditions may vary depending upon factors including the GC content and length of the oligomer, the degree of similarity between the oligomer sequence and sequences of non-target nucleic acids that may be present in the test sample, and the target sequence. Hybridization conditions include the temperature and the composition of the hybridization reagents or solutions. Preferred hybridization assay conditions for amplifying and/or detecting target nucleic acids derived from one or more virus strains of the specified influenza A virus types with the probes of the present invention correspond to a temperature of about 60° C. when the salt concentration is in the range of about 0.6-0.9 M. Specific hybridization assay conditions are set forth infra in the Examples section. Other acceptable stringent hybridization conditions could be easily ascertained by those having ordinary skill in the art.

By "assay conditions" is meant conditions permitting stable hybridization of an oligonucleotide to a target nucleic acid. Assay conditions do not require preferential hybridization of the oligonucleotide to the target nucleic acid.

"Label" or "detectable label" refers to a moiety or compound joined directly or indirectly to a probe that is detected or leads to a detectable signal. Direct joining may use covalent bonds or non-covalent interactions (e.g., hydrogen bonding, hydrophobic or ionic interactions, and chelate or coordination complex formation) whereas indirect joining may use a bridging moiety or linker (e.g., via an antibody or additional oligonucleotide(s), which amplify a detectable signal. Any detectable moiety may be used, e.g., radionuclide, ligand such as biotin or avidin, enzyme, enzyme substrate, reactive group, chromophore such as a dye or particle (e.g., latex or metal bead) that imparts a detectable color, luminescent compound (e.g. bioluminescent, phosphorescent or chemiluminescent compound), and fluorescent compound (i.e., fluorophore). Embodiments of fluorophores include those that absorb light in the range of about 495 to 650 nm and emit light in the range of about 520 to 670 nm, which include those known as FAM™, TET™, CAL FLUOR™ (Orange or Red), and QUASAR™ compounds. Fluorophores may be used in combination with a quencher molecule that absorbs light when in close proximity to the fluorophore to diminish background fluorescence. Such quenchers are well known in the art and include, e.g., BLACK HOLE QUENCHER™ (or BHQ™) or TAMRA™ compounds. Particular embodiments include a "homogeneous detectable label" that is detectable in a homogeneous system in which bound labeled probe in a mixture exhibits a detectable change compared to unbound labeled probe, which allows the label to be detected without physically removing hybridized from unhybridized labeled probe (e.g., U.S. Pat. Nos. 5,283,174, 5,656,207 and 5,658,737). Particular homogeneous detectable labels include chemiluminescent compounds, more preferably acridinium ester ("AE") compounds, such as standard AE or AE derivatives which are well known (U.S. Pat. Nos. 5,656,207, 5,658,737, and 5,639,604). Methods of synthesizing labels, attaching labels to nucleic acid, and detecting signals from labels are well known (e.g., Sambrook et al., *Molecular Cloning, A Laboratory Manual*, 2nd ed. (Cold Spring Harbor Laboratory Press, Cold Spring Harbor, N. Y., 1989) at Chapt. 10, and U.S. Pat. Nos. 5,658,737, 5,656,207, 5,547,842, 5,283,174, and 4,581,333, and EP Pat. App. 0 747 706). Particular methods of linking an AE compound to a nucleic acid are known (e.g., U.S. Pat. Nos. 5,585,481 and 5,639,604, see column 10, line 6 to column 11, line 3, and Example 8). Particular AE labeling positions are a probe's central region and near a region of A/T base pairs, at a probe's 3' or 5' terminus, or at or near a mismatch site with a known sequence that is the probe should not detect compared to the desired target sequence. Other detectably labeled probes include TaqMan probes, molecular torches and molecular beacons. TaqMan probes include a donor and acceptor label wherein fluorescence is detected upon enzymatically degrading the probe during amplification in order to release the fluorophore from the presence of the quencher. Molecular torches and beacons exist in open and closed configurations wherein the closed configuration quenches the fluorophore and the open position separates the fluorophore from the quencher to allow fluorescence. Hybridization to target opens the otherwise closed probes.

Sequences are "sufficiently complementary" if they allow stable hybridization of two nucleic acid sequences, e.g., stable hybrids of probe and target sequences, although the sequences need not be completely complementary. That is, a "sufficiently complementary" sequence that hybridizes to another sequence by hydrogen bonding between a subset series of complementary nucleotides by using standard base pairing (e.g., G:C, A:T or A:U), although the two sequences may contain one or more residues (including abasic positions) that are not complementary so long as the entire sequences in appropriate hybridization conditions to form a stable hybridization complex. Sufficiently complementary sequences are preferably at least about 80%, more preferably at least about 90%, and most preferably completely complementary in the sequences that hybridize together. Appropriate hybridization conditions are well known to those skilled in the art, can be predicted based on sequence composition, or can be determined empirically by using routine testing (e.g., Sambrook et al., *Molecular Cloning, A Laboratory Manual,* $2^{nd}$ ed. at §§ 1.90-1.91, 7.37-7.57, 9.47-9.51 and 11.47-11.57, particularly §§ 9.50-9.51, 11.12-11.13, 11.45-11.47 and 11.55-11.57).

"Consisting essentially of" means that additional component(s), composition(s) or method step(s) that do not materially change the basic and novel characteristics of the compositions and methods described herein may be included in those compositions or methods. Such characteristics include the ability to detect an influenza virus A nucleic acid sequence present in a sample with specificity that distinguishes the influenza virus nucleic acid from at least 50 other known respiratory pathogens, preferably at a sensitivity that detects at least 1.7 to 2.7 log copies of the influenza virus, within about 45 min from the beginning of an amplification reaction that makes amplified viral sequences that are detected.

Unless defined otherwise, all scientific and technical terms used herein have the same meaning as commonly understood by those skilled in the relevant art. General definitions may be found in technical books relevant to the art of molecular biology, e.g., *Dictionary of Microbiology and Molecular Biology*, 2nd ed. (Singleton et al., 1994, John Wiley & Sons, New York, N.Y.) or *The Harper Collins Dictionary of Biology* (Hale & Marham, 1991, Harper Perennial, New York, N.Y.). Unless mentioned otherwise, techniques employed or contemplated herein are standard methodologies well known to one of ordinary skill in the art. The examples included herein illustrate some particular embodiments.

Description

Compositions that include nucleic acid oligomers that function in target capture, amplification, and detection of nucleic acids and methods for detecting swine H1N1 influenza A virus, seasonal H1 influenza A virus and/or seasonal H3 influenza A virus nucleic acids present in a biological sample are disclosed herein.

To select target sequences appropriate for use in the tests to detect swine H1N1 influenza A virus, known swine H1N1 influenza A virus RNA or DNA sequences that encode either the H1 antigen from the swine H1N1 influenza A virus or the NP protein from the swine H1N1 influenza A virus, including partial or complementary sequences (available at publicly accessible databases, e.g., GenBank), are aligned by matching regions of identical or similar sequences and compared. Once the sequence homology among the multiple strains is determined, sequences are chosen for areas which have a high homology among the many strains of swine H1N1 influenza A virus, and primers and probes are designed according to conventional primer and probe design methods. It is important to note, however, that because viruses have a high mutation rate, on occasion the conventional tenets of primer and probe design are compromised on. The primers and probes are then tested against a target nucleic acid under standard reaction conditions to determine reactivity and specificity. If the probes and primers are not effective against the target sequence in singleplex mode, they are not chosen for further testing. Effectiveness is determined by the sensitivity of the oligonucleotides and the specificity of the oligonucleotides. The sequences which are effective in singleplex mode are subsequently tested in a multiplex assay, which included an Internal Control sequence, primers and probe(s). Various target sequences representing multiple swine H1N1 influenza A strains may be tested in singleplex and/or multiplex mode.

Target sequences appropriate for use in detecting the swine H1N1 influenza A virus are preferably not complementary to sequences in the seasonal H1 Influenza A virus or the seasonal H3 Influenza A virus, so that a positive detection of the swine H1N1 influenza A target sequence is specific to the swine H1N1 influenza A virus and do not also detect the other virus types.

In particular, oligonucleotides target the H1 nucleic acid in the regions corresponding to nucleotides 71-244, 316-408, 445-621, 722-868, 921-1121, 1215-1407, or 1525-1669 of GenBank Sequence GU984417.1 version GI:290873747 submitted Mar. 10, 2010 (SEQ ID NO:103), are chosen as primers and probes. Alternatively, oligonucleotides from the sequence encoding the NP protein in the regions corresponding to nucleotides 38-272, 272-413, 459-648, 768-912, 969-1061, or 1190-1328, of 599:A/Thailand/CU-B5/2009 (SEQ ID NO:104) are chosen as primers and probes.

Although oligonucleotides were selected from "regions corresponding to" a single viral nucleic acid sequence, the invention is not limited to oligonucleotides target only the referenced specific sequences or to the particular cited virus strains. It will be understood by those skilled in the art in possession of this disclosure how to align and determine corresponding regions between various strains of swine H1N1 influenza A virus, seasonal H1 influenza A virus and/or seasonal H3 influenza A virus. In addition, useful primers and probes are not limited to the specific sequences listed herein, but may have 1, 2, 3, 4, 5, 6, 7, or 8 nucleotide substitutions within the conserved region when compared with the database sequence.

To select target sequences appropriate for use in the tests to detect the seasonal H1 Influenza virus A, seasonal H1 Influenza virus A RNA or DNA sequences that encode a the H1 antigen, including partial or complementary sequences (available at publicly accessible databases, e.g., GenBank) are aligned by matching regions of identical or similar sequences and compared. Similarly, to select target sequences appropriate for use in the tests to detect the seasonal H3 Influenza virus A, seasonal H3 Influenza virus A RNA or DNA sequences that encode a the H3 antigen, including partial or complementary sequences (available at publicly accessible databases, e.g., GenBank) are aligned by matching regions of identical or similar sequences and compared. As with the swine H1N1 influenza A virus sequences, the primers and probes for the seasonal H1 Influenza A or seasonal H3 Influenza A are selected from regions having high homology among the various strains of seasonal H1 Influenza A or seasonal H3 Influenza A viruses.

The primers and probes are tested in singleplex then multiplex modes. As with the swine H1N1 influenza A virus primers and probes, the seasonal flu primers and probes are tested against multiple strains of seasonal H1 Influenza A virus and seasonal H3 Influenza A virus.

In particular, oligonucleotides from DNA that encodes the H1 antigen of the seasonal H1 Influenza A virus in the regions corresponding to nucleotides 658-785, 808-968, 1064-1281 of GenBank Sequence CY030230.1 version GI:168805690, submitted May 9, 2008 (SEQ ID NO:105), are chosen as primers and probes for seasonal H1 Influenza A detection. Also, oligonucleotides from the H3 antigen in the regions corresponding to nucleotides 4-179, 157-294, 254-419, 342-510, 632-804, 748-853, 841-1084, 886-1085, 1062-1170, 1141-1321, 1281-1389, 1325-1480, 1406-1478, or 1488-1668 of GenBank Accession number EU103640.1 version GI:156691489, submitted Mar. 26, 2008 (SEQ ID NO:106), are chosen as primers and probes for H3 Influenza A detection.

Although sequence comparisons may be facilitated by use of computer-performed algorithms, one of ordinary skill can perform the comparisons manually and visually. Portions of sequences for each viral target that contained relatively few sequence changes between the compared individual viral sequences are chosen as a basis for designing synthetic oligomers for use in the methods described herein.

Exemplary oligonucleotide sequences for detecting the swine H1N1 Influenza A target are described in Table 1, exemplary oligomer sequences for detecting the seasonal H1 Influenza A Virus target are described in Table 2, and exemplary oligomer sequences for detecting the seasonal H3 Influenza A Virus target are described in Table 3.

Those skilled in the art will recognize that oligomers identified as having a preferred function in target capture have target-specific portions and optionally include tail portions which may be deleted or substituted with other sequences or binding moieties. Such tail portions may be nucleotide or non-nucleotide linkers by which labels or other ancillary molecules used in signaling amplification are attached to the oligonucleotide. For example, for clarity, sequences shown below that include a 5' fluorophore ("F") and a 3' quencher compound ("Q") are written to show the presence of F and Q molecules. Those skilled in the art will appreciate that the ancillary molecules may take many forms, and be placed in many locations in a nucleic acid molecule, such as at either end or with one or more of the F or Q molecules bound to a nucleotide in the middle of the nucleic acid sequence. One of skill in the art will also recognize that these molecules are not required for the target specific oligonucleotide to function in embodiments of the claimed methods or compositions of this application.

TABLE 1

Oligomer Sequences Targeting Swine H1N1 *Influenza A Virus*

| SEQ ID | Sequence | Preferred Function | Direction |
|---|---|---|---|
| 1 | AAGTCGAAACCCAGGAAAC | Primer | forward |
| 2 | CATGCCCACTTGCTACTG | Primer | reverse |
| 3 | F-CATACACACAAGCAGGCAGGCA-Q | Probe | reverse |
| 4 | F-AAGACCTCATTTTCCTGGCACGGT-Q | Probe | forward |
| 5 | CACGGTCAGCACTCATTC | Primer | forward |
| 6 | TTCAAAGTCATGCCCACTTG | Primer | reverse |

TABLE 1 -continued

Oligomer Sequences Targeting Swine H1N1 *Influenza A Virus*

| SEQ ID | Sequence | Preferred Function | Direction |
|---|---|---|---|
| 7 | F-ATCAGTTGCACATAAATCCTGCCTG-Q | Probe | forward |
| 8 | ATTGGTGGAATCGGGAGATT | Primer | forward |
| 9 | AGGTATTTATTTCTTCTCTCATC | Primer | reverse |
| 10 | F-TCCAAATGTGCACTGAACTCAAACTC-Q | Probe | forward |
| 11 | F-TAGTCGTCCATCATAATCACTGAGTTT-Q | Probe | reverse |
| 12 | TGGCGTCTCAAGGCACC | Primer | forward |
| 13 | TTCCACCAATCATTCTTCCGA | Primer | reverse |
| 14 | F-ATCATATGAACAAATGGAGACTGGTGG-Q | Probe | forward |
| 15 | F-CGCCAGGATGCCACAGAAATCAGA-Q | Probe | forward |
| 16 | F-TGCTCTGATTTCTGTGGCATCCTGG-Q | Probe | reverse |
| 17 | TAGAAGAGCATCCCAGTGC | Primer | forward |
| 18 | CCATTGTTTGCTTGGCGC | Primer | reverse |
| 19 | F-AAGGACCCTAAGAAAACAGGAGGACC-Q | Probe | forward |
| 20 | F-TTCTTCTTTGTCATAAAGGATGAGTTCTC-Q | Probe | reverse |
| 21 | CAACCTGAATGATGCCACAT | Primer | forward |
| 22 | TCGGTCATTGATTCCACGTT | Primer | reverse |
| 23 | F-AGAGCGCTTGTTCGCACCGGAAT-Q | Probe | forward |
| 24 | F-CAGAATGTGCTCTCTAATGCAAGGTTC-Q | Probe | forward |
| 25 | F-TCATTCTGATTAACTCCATTGCTATTGT-TCC-Q | Probe | reverse |
| 26 | AGTGGTCAGCCTGATGAGA | Primer | forward |
| 27 | CTTAAATCTTCAAATGCAGCAG | Primer | reverse |
| 28 | F-CAAATGAAAACCCAGCTCACAAGAGTC-Q | Probe | forward |
| 29 | F-TGGCATGCCATCCACACCAATTGA-Q | Probe | forward |
| 30 | ACTGGGCCATAAGGACCA | Primer | forward |
| 31 | CCGCTGAATGCTGCCATA | Primer | reverse |
| 32 | F-AGTGGAGGAAATACCAATCAACAAAAGGC-Q | Probe | forward |
| 33 | F-CGCTGCACTGAGAATGTAGGCTG-Q | Probe | reverse |
| 34 | GCGAACAATTCAACAGACAC | Primer | forward |
| 35 | GATTTCCCAGGATCCAGC | Primer | reverse |
| 36 | F-TAGACACAGTACTAGAAAAGAATG-TAACAG-Q | Probe | forward |
| 37 | F-ATGCAATGGGGCTACCCCTCTTA-Q | Probe | reverse |
| 38 | ACGTGTTACCCAGGAGATTT | Primer | forward |
| 39 | CTTGGGGAATATCTCAAACC | Primer | reverse |
| 40 | F-TCGATTATGAGGAGCTAAGAGAGCAAT-Q | Probe | forward |
| 41 | F-ATTGCTCTCTTAGCTCCTCATAATCGA-Q | Probe | reverse |
| 42 | GTAACGGCAGCATGTCCT | Primer | forward |

TABLE 1 -continued

Oligomer Sequences Targeting Swine H1N1 *Influenza A Virus*

| SEQ ID | Sequence | Preferred Function | Direction |
|---|---|---|---|
| 43 | TAGAGACTTTGTTGGTCAGC | Primer | reverse |
| 44 | F-TGGTGAATGCCCCATAGCACGAG-Q | Probe | reverse |
| 45 | AGAATGAACTATTACTGGACAC | Primer | forward |
| 46 | GGACTGGTGTATCTGAAATG | Primer | reverse |
| 47 | F-TAGAGCCGGGAGACAAAATAACATTC-Q | Probe | forward |
| 48 | F-ACTGGAAATCTAGTGGTACCGAGATA-Q | Probe | forward |
| 49 | F-TACCAGATCCAGCATTTCTTTCCATTG-Q | Probe | reverse |
| 50 | AGCACAAAATTGAGACTGGC | Primer | forward |
| 51 | CCTGCTCATTTTGATGGTG | Primer | reverse |
| 52 | F-CAGGATTGAGGAATGTCCCGTCTA-Q | Probe | forward |
| 53 | F-ACCGTACCATCCATCTACCATCC-Q | Probe | reverse |
| 54 | ACAGTTCACAGCAGTAGGTA | Primer | forward |
| 55 | CTGGCTTCTTACCTTTTCATAT | Primer | reverse |
| 56 | F-TTGATGATGGTTTCCTGGACATTTGGA-Q | Probe | forward |
| 57 | F-TCTTCACATTTGAATCGTGGTAGTCCAAA-Q | Probe | reverse |
| 58 | F-TCATTTTCCAATAGAACCAACAGTTCGG-Q | Probe | reverse |
| 59 | GAAGCAAAATTAAACAGAGAAGAA | Primer | forward |
| 60 | TAGAGCACATCCAGAAACTGA | Primer | reverse |
| 61 | F-ATCAACAAGGATTTACCAGATTTTGGCGA-Q | Probe | forward |
| 62 | F-ACCAATGAACTGGCGACAGTTGAATAGA-Q | Probe | reverse |

The notations "F" and "Q" have been added to probe sequences in Table 1 to indicate end-labeling the probe sequences with a fluorophore and a quencher, respectively. These notations are merely exemplary showing use of the probes for TaqMan PCR.

TABLE 2

Oligomer Sequences Targeting seasonal H1 *Influenza A Virus*

| SEQ ID | Sequence | Preferred Function | Direction |
|---|---|---|---|
| 63 | AGGTTTGTTTGGAGCCATTG | Primer | forward |
| 64 | TTGTTGAATTCTTTGCCCAC | Primer | reverse |
| 65 | F-TCATTGAAGGGGGGTGGACTGGAA-Q | Probe | forward |
| 66 | F-TGGACTGGAATGGTAGATGGTTGGT-Q | Probe | forward |
| 67 | F-TCATTTTCTCAATTACAGAATTCACCTTGTTTG-Q | Probe | reverse |
| 68 | ATCATACAGAAAATGCTTATGT | Primer | forward |
| 69 | MAGCAGAGTCCAGTAGTA | Primer | reverse |

TABLE 2 -continued

Oligomer Sequences Targeting seasonal H1 *Influenza A Virus*

| SEQ ID | Sequence | Preferred Function | Direction |
|---|---|---|---|
| 70 | F-TTCACATTATAGCAGAAGATTCACCCCAG-Q | Probe | forward |
| 71 | F-ACCCCAGAAATAGCCAAAAGACCC-Q | Probe | forward |
| 72 | TTGAGGCAAATGGAAATCTAATA | Primer | forward |
| 73 | TACATTCTGGAAAGGAAGACT | Primer | reverse |
| 74 | F-AGTAGAGGCTTTGGATCAGGAATCATC-Q | Probe | forward |
| 75 | F-TGTTTATAGCTCCCTGAGGTGTTTGACA-Q | Probe | reverse |
| 76 | F-CATTGGTGCATTTGAGGTGATGATTCCT-Q | Probe | reverse |

The notations "F" and "Q" have been added to probe sequences in Table 2 to indicate end-labeling the probe sequences with a fluorophore and a quencher, respectively. These notations are merely exemplary showing use of the probes for TaqMan PCR.

TABLE 3

Oligomer Sequences Targeting seasonal H3 *Influenza A Virus*

| SEQ ID | Sequence | Preferred Function | Direction |
|---|---|---|---|
| 77 | ACTAATGCTACTGAGCTGGT | Primer | forward |
| 78 | CTTATTTTGGAAGCCATCACA | Primer | reverse |
| 79 | F-ATCCTTGATGGAGAAAACT GCACACTA-Q | probe | forward |
| 80 | F-AGGGTCTCCCAATAGAGCA TCTATTAG-Q | probe | reverse |
| 81 | F-TAGTGTGCAGTTTTCTCCA TCAAGGAT-Q | probe | reverse |
| 82 | AAGACTATCATTGCTTTGAGCT | Primer | forward |
| 83 | TGAACCAGCTCAGTAGCATT | Primer | reverse |
| 84 | F-CTTCAATTTGGTCATTCGT GATTGTTTTCAC-Q | probe | reverse |
| 85 | CTCTATTGGGAGACCCTCA | Primer | forward |
| 86 | CTTTCATTGTTAAACTCCAGTG | Primer | reverse |
| 87 | F-TGTGATGGCTTCCAAAATA AGAAATGGGA-Q | probe | forward |
| 88 | TGCTCAAGCATCAGGAAGAAT | Primer | forward |
| 89 | CCCTAGGAGCAATTAGATTC | Primer | reverse |
| 90 | F-TCTACCAAAAGAAGCCAAC AAACTGTAAT-Q | probe | forward |
| 91 | F-TGCTGTTAATCAAAAGTAT GTCTCCCG-Q | probe | reverse |
| 92 | AGCTCAATAATGAGATCAGATG | Primer | forward |
| 93 | TTCCCTCCCAACCATTTTCT | Primer | reverse |
| 94 | F-CCAAATGGAAGCATTCCCA ATGACAAAC-Q | probe | forward |
| 95 | F-CAAATATGCCTCTAGTTTG TTTCTCTGG-Q | probe | reverse |
| 96 | TCTCAAAAGCACTCAAGCAG | Primer | forward |
| 97 | CTCCGCGTTGTATGACCA | Primer | reverse |
| 98 | F-CAAATCAATGGGAAGCTGA ATAG(A/G)TTG-Q | probe | forward |
| 99 | CCTGGAGAACCAACATACAA | Primer | forward |
| 100 | CAGGCATTGTCACATTTGTG | Primer | reverse |
| 101 | F-TGATCTAACTGACTCAGAA ATGAACAAACT-Q | probe | forward |
| 102 | F-ATCCTCAGCATTTTCCCTC AGTTGCT-Q | probe | reverse |

The notations "F" and "Q" have been added to probe sequences in Table 3 to indicate end-labeling the probe sequences with a fluorophore and a quencher, respectively. These notations are merely exemplary showing use of the probes for TaqMan PCR.

Although sequences are shown in Tables 1, 2, and 3 as DNA, RNA or mixed DNA/RNA sequences, the sequences are meant to include the corresponding DNA or RNA sequences, and their completely complementary DNA or RNA sequences. Particular embodiments of oligomers may include one or more modified residues affecting the backbone structure (e.g., 2'-methoxy substituted RNA groups), or one or more LNA monomers, preferably at 5' residues of a primer oligomer, or may include a non-nucleotide linker to attach a label to the oligomer. For example, oligomers that function as probes for RNA targets may be synthesized with 2-methoxy substituted RNA groups to promote more stable hybridization between probe and target sequences. Embodiments include oligomers of the sequences above synthesized with 2'-methoxy substituted RNA groups and having a non-nucleotide linker (as described in U.S. Pat. No. 5,585,481) between residues.

Particular embodiments of target capture oligomers include a target-specific sequence that binds specifically to the swine H1N1 influenza A virus, seasonal H1 Influenza A virus or seasonal H3 Influenza A target nucleic acid and a covalently linked "tail" sequence used in capturing the hybridization complex containing the target nucleic acid to an immobilized sequence on a solid support. Particular embodiments of capture oligomers include at least one 2' methoxy linkage. Embodiments of capture oligomers may include the target-specific sequence that binds to a swine H1N1 influenza A virus, seasonal H1 Influenza A virus or seasonal H3 Influenza A genomic sequence attached to another binding moiety, e.g., a biotinylated sequence that binds specifically to immobilized avidin or streptavidin. The tail sequence or binding moiety binds to an immobilized probe (e.g., complementary sequence or avidin) to capture the hybridized target and separate it from other sample components by separating the solid support from the mixture.

Primer sequences, including promoter primer sequences, bind specifically to the target nucleic acid or its complementary sequence and may contain additional sequences that are not target-specific, e.g., the promoter sequence in a promoter primer. A target-specific sequence, with or without an attached promoter sequence, may serve as an amplification oligomer in a variety of in vitro amplification processes. Embodiments of the swine H1N1 influenza A virus, seasonal H1 Influenza A virus or seasonal H3 Influenza A virus assays may use amplification methods that require multiple cycling reaction temperatures, such as PCR (U.S. Pat. Nos. 4,683,195, 4,683,202, and 4,800,159), or may be substantially isothermal as in transcription associated amplification methods, such as TMA or NASBA (e.g., U.S. Pat. Nos. 5,399,491, 5,480,784, 5,824,518, 5,888,779, 5,786,183, 5,437,990, 5,130,238, 4,868,105, and 5,124,246, and PCT Nos. WO 8801302 and WO 8810315). Particular embodiments of the swine H1N1 influenza A virus, seasonal H1 Influenza A virus or seasonal H3 Influenza A virus assays use PCR-based or TMA-based amplification systems that are detected during the amplification process (i.e., real time detection) by including probes that emit distinguishable fluorescent signals when the probe is bound to the intended target sequence made during the amplification process. Particular probes for real time detection include those referred to as "TaqMan" (e.g., U.S. Pat. No. 5,691,146 Mayrand, U.S. Pat. No. 5,538,848 Livak), "molecular beacon" or "molecular switch" probes (e.g., U.S. Pat. Nos. 5,118,801 and 5,312,728, Lizardi et al., U.S. Pat. Nos. 5,925,517 and 6,150,097, Tyagi et al., Giesendorf et al., 1998, Clin. Chem. 44(3):482-6) and "molecular torch" probes (e.g., U.S. Pat. Nos. 6,835,542 and 6,849,412, Becker et al.). Generally, such probes include a reporter dye attached to one end of the probe oligomer (e.g., FAM™, TET™, JOE™, VIC™) and a quencher compound (e.g., TAMRA™, BLACK HOLE QUENCHERS™ or non-fluorescent quencher) attached to the other end of the probe oligomer, and signal production depends on whether the two ends with their attached compounds are in close proximity or separated.

The assay to detect one or more of the specified influenza viruses in a sample includes the steps of amplifying a target region in the target influenza virus nucleic acid contained in a sample by using amplification oligomers or primers specific for the intended target region, and then detecting the amplified nucleic acid. In some aspects, the detection step uses a detection probe oligomer with a target hybridizing sequence that is hybridized to the target nucleic acid and/or amplification products generated therefrom. Preferred assays use a PCR and detection is during the amplification reaction using a detection probe oligomer. For detection, the amplified nucleic acid may be labeled and bound to an unlabeled probe, but particular embodiments bind a labeled probe to the amplified nucleic acid. A particular embodiment for real-time detection uses a labeled probe that is detected in a homogeneous system. In some aspects, the detection step is performed using a technique such as gel electrophoresis, sequencing or mass spectrometry (e.g., U.S. Pat. Nos. 6,316,769, 6,011,496 and 7,170,050 and US App. Pub. No. 2007/0087340).

Generally, the target influenza virus nucleic acid is separated from other sample components before the amplification step. This may be done by capturing the influenza virus nucleic acid by using a target-capture oligomer that binds to the target influenza virus nucleic acid, or by using non-specific methods of purifying nucleic acid from a sample (e.g., U.S. Pat. Nos. 5,234,809, 5,705,628, 6,534,262 and 6,939,672, and International App. Pub. No. WO 2008/016988). Particular embodiments use a target-specific capture oligomer in a capturing step (U.S. Pat. Nos. 6,110,678, 6,280,952 and 6,534,273). Embodiments of capture probes include those specific for swine H1N1 Influenza A virus, those specific for the seasonal H1 Influenza A virus, and those specific for the seasonal H3 Influenza A virus. Preferably, the target capture probes are specific for the subset of nucleic acids in a sample that are H1N1, seasonal H1 or seasonal H3. Embodiments of the probes specific for these viruses include a $dT_{0\text{-}3}dA_{12\text{-}30}$ tail portion for hybridization to a complementary immobilized probe sequence. Some embodiments of the probes include those wherein the nucleic acid tail portion is a left-handed nucleic acid tail and hybridizes with an immobilized probe that is a left-handed nucleic acid, while other embodiments use right-handed tails and immobilized probes. Preferably, the influenza viral nucleic acids are separated from other sample components by hybridizing the influenza nucleic acids to the target-hybridizing portion of the capture probe and hybridizing the tail portion of the capture probe to an immobilized probe that is attached to a solid support. This complex of capture probe, its target influenza virus nucleic acid, and an immobilized probe facilitate separation of the influenza virus nucleic acid from other sample components, and optional washing steps may be used to further purify the captured viral nucleic acid. Preferred solid supports include magnetic particles, though other solid support work well, as is known in the art. Alternatively, non-specific separation of viral RNA from other sample components is performed by adhering nucleic acids reversibly to a solid support, followed by washing and elution of the adhered nucleic acids into a substantially aqueous solution (e.g., using a MagNA Pure LC System (Roche) and the MagNA Pure Total Nucleic Acid Isolation Kit (Roche) or a NucliSENS easy MAG System (bioMérieux and the Automated Magnetic Extraction Reagents (bioMérieux) or comparable nucleic acid extraction instrument(s) and/or reagent kit(s)).

Amplifying the influenza virus target region using two primers may be accomplished using a variety of known nucleic acid amplification reactions, but preferably uses a PCR amplification (U.S. Pat. Nos. 4,683,195, 4,683,202, and 4,800,159, Mullis et al.) to produce multiple DNA strands by using thermocycling reactions that separate dsDNA and primers specific for portions of the separated strands to make additional dsDNA molecules by using a DNA polymerase. Well known variations of the basic PCR method may also be used, e.g., reverse-transcriptase PCR that uses RT to produce a cDNA from an RNA template, and then the DNA is amplified by PCR cycles, or PCR coupled with real-time detection, both of which are sometimes referred to as RT-PCR.

Another embodiment of the influenza virus assay uses transcription-associated amplification reaction, such as TMA (described in detail in U.S. Pat. Nos. 5,399,491 and 5,554,516). A TMA-based assay produces many RNA transcripts (amplicons) from a single copy of target nucleic acid or cDNA therefrom, and the amplicons are detected to indicate the presence of the target influenza virus in the sample. Briefly, in one example of a TMA-based assay, a promoter-primer hybridizes specifically to the target sequence and reverse transcriptase (RT) that includes RnaseH activity creates a first strand cDNA by extension from the 3' end of the promoter-primer and digests the template strand. The cDNA is then bound by a second primer and a new strand of DNA is synthesized from the end of the second primer using RT to create a double-stranded DNA (dsDNA) containing a functional promoter sequence. RNA polymerase specific for that promoter binds to the promoter sequence and multiple RNA transcripts are produced, which each can act as a template for additional sequence replication using the same steps used for the initial template. Thus, large amounts of single-stranded amplified product are made using substantially isothermal reaction conditions.

Preferably, isolated influenza virus nucleic acid is then amplified for specific target sequences contained the viral genome by using PCR or TMA amplification, and the amplification products are detected after completion of the amplification reaction or during amplification (i.e., real-time detection). For real-time detection, some embodiments may use a fluorophore-labeled probe (e.g., TaqMan, molecular beacon) that emits a detectable signal only when the probe is hybridized to its target sequence, and fluorescence is detected using standard fluorometry. Generally, assays detect at least two different probes (with different 5' fluorophores): an influenza virus-specific probe and an IC-specific probe. Fluorescence is detected by using a system that incubates the reactions and detects fluorescence at different wavelengths at time intervals during the reaction (e.g., DNA Engine OPTICON™ 2 system or CHROMO4™ Real-Time PCR Detector, Bio-Rad Laboratories, Inc., Hercules, Calif.). Real-time detected fluorescent signals in each channel are analyzed using standard methods. For example, detected signals are normalized to generate a best-fit curve to the data points for each reaction (relative fluorescence vs. time) and results are reported as the time of emergence when the signal met or exceeded a pre-set level.

Real-time reverse-transcriptase PCR-based assays (RT-PCR) are performed by using 50-500 nM solutions and 0.2 pmol/μl of probe in a 50 μl reaction that includes standard PCR reaction components. Incubation is performed using: 48° C. for 30 min, 95° C. for 10 min, then 45 cycles of 95°

C. for 15 sec and cooling, and finally 60° C. for 1 min. Amplification and detection of the molecular beacon probe hybridized to its target amplified product are performed by using an open channel system (CHROMO4™, Bio-Rad Laboratories, Inc.) for real-time fluorescence detection, with fluorescent signal readings taken at each of the 45 cycles. Real-time fluorescence signals are analyzed and detection of the analytes calculated from the fluorescence emergence curves by using standard methods.

The methods for detecting influenza virus nucleic acid include a detecting step that uses at least one probe that binds specifically to the amplified influenza virus product (RNA or DNA amplicons). Preferably, the probe is labeled and produces a signal detected in a homogeneous system, i.e., without separation of bound probe from unbound probe. Particular probes are labeled with a fluorescent compound which emits a detectable signal only when the probe is bound to its target, e.g., TaqMan, molecular switch, beacon, or torch probes. Other particular probes may be labeled with an acridinium ester (AE) compound from which a chemiluminescent signal is produced and detected in a homogeneous system (substantially as described in detail in U.S. Pat. Nos. 5,283,174, 5,656,744, and 5,658,737).

Particular embodiments of assays for detection of swine H1N1 Influenza A virus, seasonal H1 Influenza A virus, and/or seasonal H3 Influenza A virus nucleic acids include an internal control (IC) nucleic acid that is amplified and detected by using IC-specific primers and probe in the same reaction mixtures used for influenza virus nucleic acid amplification and detection (referred to herein as IC primers and IC probe). Amplification and detection the IC-specific sequence demonstrates that assay reagents and conditions are properly used even when no influenza virus-specific signal is detected for a tested sample (i.e., negative samples). The IC may be used as an internal calibrator for the assay that provides a quantitative result. A particular IC embodiment is a randomized sequence derived from a naturally occurring source that is not an influenza virus (e.g., HIV).

Probes for detection of IC amplicons include any oligomer of at least ten residues that hybridizes specifically to a contiguous sequence contained in the IC sequence or its complement (DNA or RNA) under assay conditions described herein. A particular IC-specific probe is exemplified by an oligomer labeled with a fluorescent compound at one end and a quencher at the other end. In particular embodiments that include an IC in an assay, the IC is treated throughout the assay similar to the intended analyte. For example, when a target capture step is used for purification of the influenza virus nucleic acid target in a sample, the target capture step includes a capture oligomer specific for the IC to purify the IC from a mixture that includes the target influenza virus nucleic acid and other sample components.

In general, methods used to demonstrate amplification and detection of swine H1N1 influenza A virus, seasonal H1 Influenza virus A, or seasonal H3 Influenza Virus A nucleic acid by using the compositions described herein in steps that include some sample preparation to isolate the influenza virus or its released nucleic acid from some other non-analyte components of the sample, followed by nucleic acid amplification of the target viral sequences, and detection of the amplified products to provide information that identifies the amplified sequence(s) which indicate the presence of the target influenza virus(es) in the sample.

EXAMPLE 1

Extraction and Storage of Samples

Samples are taken from nasopharyngeal swabs (NPS) of patients presenting flu-like symptoms and the samples are each placed into approximately 3 ml of viral transport medium (for example M4, M4RT, M5, or M6 media (Remel), UVT media (Becton Dickinson), or UTM media (Copan)). Samples were refrigerated for transport at 2-8° C., and stored at that temperature for up to approximately 72 hours before processing. Samples which needed longer storage were stored at ≤−70° C. Nucleic acids were extracted from samples using standard laboratory methods to isolate nucleic acids (e.g., MagNA Pure LC System using the Total Nucleic Acid Isolation Kit (Roche) or the NucliSENS easyMAG System using the Automated Magnetic Extraction Reagents (bioMérieux)). A positive control sample is included which has a target sequence for each of the tested viral strains. That is, if the swine H1N1 influenza A virus is to be tested, a swine H1N1 influenza A virus target sequence is included. Here, the positive controls were pooled RNA transcript from a portion of an HA gene or of an NP gene for each of the subtypes of influenza. In addition, a negative control including the viral transport medium, but not including a target sequence, and Internal Controls were extracted alongside the samples.

EXAMPLE 2

The Uniplex Reactions

Once the primers are chosen, as described above, the primers are tested against its target in a PCR amplification assay.

Materials: PCR Master Mix containing about 2 mM $MgCl_2$ and about 0.8 mM dNTPs when diluted to 1× (Roche); Taq DNA Polymerase (Roche); RNAse Inhibitor 40 u/μL; Reverse Transcriptase 10 u/μL; Influenza A/Jianxi/160/05(H1N1) $1\times10^{5.5}$ $TCID_{50}$/ml (seasonal H1 Influenza A virus strain); Influenza A/Hong Kong/218/08 (H3N2) $1\times10^{5.25}$ $TCID_{50}$/ml (seasonal H3 Influenza A virus strain); Influenza A H1N1-Swine Flu Clinical specimen (swine H1N1 influenza A virus strain); an Internal RNA Control nucleic acid; and Remel M4-Viral Transport Medium (VTM). For most uniplex reactions, primers were used at approximately 50 μM and probes at approximately 10 μM.

Procedure: Extraction and dilution of samples was completed on the easyMAG and 0.200 ml input and 55 μL elution volumes using the generic protocol 2.0.1 (available from bioMérieux). 63.2 μL of Influenza A/Jiangxi/160/05 (H1N1)+136.8 μL VTM=200 μL of $1\times10^5$ $TCID_{50}$/ml; and 84.4 μL of Influenza A/Hong Kong/218/06 (H3N2) $1\times10^{5.25}$ $TCID_{50}$/ml+65.6 VTM=150 μL of $1\times10^5$ $TCID_{50}$/ml. 180 μL VTM is added to 12 sample vessel wells and 20 μL of each of the above dilutions were added to 6 of the wells. 200 μL of H1N1 Swine clinical specimen was added to 6 wells. 180 μL of VTM was added to the final 6 wells and 20 μL of previously prepared RNA Internal Control (IC) was added to each of the wells. Each of the 6 extractions per subtype is mixed and then aliquoted into 6×50 μL samples for use, and then stored at −≤70° C.

Mixing the Primers and Probes: The primers and probes designed as described above are synthesized by means known to those of skill in the art. The primers and probes are mixed prior to the testing. For example, when testing the primers and probes targeting the NP gene of swine H1N1 influenza A virus from Table 1, (SEQ ID NOS:1, 2, 5, 6, 8, 9, 12, 13, 17, 18, 21, 22, 26, 27, 30 or 31 for primers and SEQ ID NOS:3, 4, 7, 10, 11, 14-16, 19, 20, 23-25, 28, 29, 32 or 33 for probes) the following mixes are made. The same is done for the primers and probes of Tables 1-3 that target the HA gene of the swine H1N1 influenza A virus, seasonal H1 influenza A virus and seasonal H3 influenza A virus.

| MiniMix: | |
|---|---|
| 2x PCR Master Mix | 12.5 μL |
| Forward Primer | 0.100 |
| Reverse Primer | 0.100 |
| Water | 5.25 |
| Total | 17.95 |

| Supermix: | |
|---|---|
| Minimix | 17.95 μL |
| Probe | 0.500 |
| Reverse Transcriptase | 0.300 |
| RNase Inhibitor | 0.25 |
| Taq 5 u/μL | 1 |
| Total | 20 |

Under this general protocol, the various probes can be labeled with any of the fluorescent labels. However, in the present example, the probes targeting seasonal H1 Influenza A virus were detected in the FAM channel (520 nm peak), probes targeting seasonal H3 Influenza A virus in the TET channel (561 nm peak), probes targeting the swine H1N1 influenza A virus in the TX Red channel (651 nm peak), and the internal control in the Cy5 channel (667 nm peak). In the present instance, the SEQ ID NO:3 probe was not detected in the FAM, CY5 or TET channels, but was detected in the TX Red channel. Detection probe oligomers can be labeled with a variety of different fluorescent labels, and are not limited to these shown in the examples. Combinations of primers and probes for a swine NP uniplex reaction included, SEQ ID NOS; 1 & 2 with 3 and/or 4; 5-7; 8 & 9 with 10 and/or 11; 12 & 13 with 14, 15 and/or 16; 17 & 18 with 19 and/or 20; 21 & 22 with 23, 24 and/or 25; 26 & 27 with 28 and/or 29; and 30 & 31 with 32 and/or 33. The protocol for thermocycling is as follows: 42° C. for 30 min, 95° C. for 10 min, 5 cycles of 95° C. for 30 sec, 55° C. for 1 min, 45 cycles of 95° C. for 1 min (detection at this step).

Using a primer probe combination of SEQ ID NOS:1-3, the following results were obtained:

TABLE 4

| Sample | TX Red (Ct) |
|---|---|
| Seasonal H1 Influenza A | 28.9 |
| Seasonal H3 Influenza A | — |
| Swine H1N1 Influenza A | 16.36 |
| Negative Control | — |
| water | — |

Here, SEQ ID NOS:1-3 detected Swine H1N1 Influenza A virus, however, there was also some cross reactivity with the seasonal H1 Influenza A virus. Therefore, SEQ ID NOS:1-3 are useful for generally detecting the presence of influenza A viruses. However, if the objective is to selectively detect and differentiate influenza types, this combination would show cross reactivity with seasonal influenza A viruses, making data interpretation difficult.

In contrast, other primer and probe sets were more specific. Table 5 includes results for SEQ ID NOS:1, 2 & 4; 1, 2 & 7; 3, 5 & 6; 5, 6 & 7; 8, 9 & 10; and 8, 9 & 11, indicating specificity by means of the TX Red values.

TABLE 5

| Primer/Probe | Sample | TX Red (Ct) |
|---|---|---|
| SEQ ID NOS: 1, 2 & 4 | Seasonal H1 Influenza A | — |
| | Seasonal H3 Influenza A | — |
| | Swine H1N1 Influenza A | 17.67 |
| | Negative Control | — |
| | water | — |
| SEQ ID NOS: 1, 2 & 7 | Seasonal H1 Influenza A | — |
| | Seasonal H3 Influenza A | — |
| | Swine H1N1 Influenza A | 17.88 |
| | Negative Control | — |
| | water | — |
| SEQ ID NOS: 3, 5 & 6 | Seasonal H1 Influenza A | 27.78 |
| | Seasonal H3 Influenza A | — |
| | Swine H1N1 Influenza A | 17.52 |
| | Negative Control | — |
| | water | — |
| SEQ ID NOS: 5-7 | Seasonal H1 Influenza A | — |
| | Seasonal H3 Influenza A | — |
| | Swine H1N1 Influenza A | 18.55 |
| | Negative Control | — |
| | water | — |
| SEQ ID NOS: 8-10 | Seasonal H1 Influenza A | — |
| | Seasonal H3 Influenza A | 33.09 |
| | Swine H1N1 Influenza A | 19.13 |
| | Negative Control | — |
| | water | — |
| SEQ ID NOS: 8, 9 & 11 | Seasonal H1 Influenza A | — |
| | Seasonal H3 Influenza A | — |
| | Swine H1N1 Influenza A | 19.02 |
| | Negative Control | — |
| | water | — |

Similar uniplex tests were conducted for each of the primer and probe sets described above in Tables 1-3.

EXAMPLE 3

Reactivity and Specificity of the PCR-based Swine H1N1 Influenza A Virus Singleplex Assay, the Seasonal H1 Influenza A Virus Singleplex Assay, or the Seasonal H3 Influenza A Virus Singleplex Assay with the Seasonal H1 Influenza A Virus and the Seasonal H3 Influenza A Virus This example demonstrates the reactivity and specificity of the PCR-based swine H1N1 influenza A singleplex assay, the seasonal H1 Influenza A singleplex assay, or the seasonal H3 Influenza A singleplex assay, with the seasonal H1 Influenza A virus and the seasonal H3 Influenza A virus, which specifically detected the intended viral target for each test. The PCR-based swine H1N1 influenza A virus assay, seasonal H1 Influenza A virus assay, and the seasonal H3 Influenza A virus assay were performed substantially as described in Example 2.

An IC RNA was included in all of the tests to demonstrate that the assay conditions and amplification and detection steps were performed appropriately to detect the IC target (or any cross-reactive target) in the sample.

Each sample containing a known virus was tested independently using the PCR-based swine H1N1 influenza A virus, seasonal H1 Influenza A virus or the seasonal H3 Influenza A virus test with the same IC. Separate swine H1N1 influenza A virus, seasonal H1 Influenza A virus, and seasonal H3 Influenza A virus nucleic acid assays were performed simultaneously under the same conditions using positive control samples that contained the relevant virus targets.

Positive controls included fourteen sources of H1N1 influenza A virus (which may or may not be a swine H1N1 influenza A virus as denoted below) and 15 sources of seasonal H3 Influenza A virus, each tested individually at $10^5$ and $10^2$ copies per reaction (samples were obtained from American Type Culture Collection (ATCC) accession numbers provided below, CDC, or the University of Wisconsin, and were grown and titered by Tricore Reference Laboratories). Positive control samples for H1N1 Influenza A virus included:

VR 1620 A/WS/33 $5\times10^{5.75}$ $TCID_{50}$/ml; at use $5\times10^{3.75}$
A/Virginia/1/08 $1\times10^4$ $TCID_{50}$/ml; at use $1\times10^2$
A/Fuijan/158/00 $1\times10^{5.5}$ $TCID_{50}$/ml; at use $1\times10^{3.5}$
A/Taiwan/42/06 $1\times10^{3.5}$ $TCID_{50}$/ml; at use $1\times10^{1.5}$
VR 997 A/New Jersey/8/76 $5\times10^{6.25}$ $TCID_{50}$/ml; at use $5\times10^{4.25}$
Brazil/1137/99 $6.8\times10^6$ $TCID_{50}$/ml; at use $6.8\times10^4$
A/Kentucky/2/06 $1\times10^{5.5}$ $TCID_{50}$/ml; at use $1\times10^{3.5}$
A/Henan/8/05 $1\times10^{4.5}$$TCID_{50}$/ml; at use $1\times10^{2.5}$
VR 98 A1/Mal/302/54 $5\times10^{7.25}$ $TCID_{50}$/ml; at use $5\times10^{5.25}$
VR 546 A1/Denver/1/57 $5\times10^{7.25}$$TCID_{50}$/ml; at use $5\times10^{5.25}$
A/Hong Kong/2506/06 $1\times10^4$ $TCID_{50}$/ml; at use $1\times10^2$
A/PR/9/34 $1\times10^8$ $TCID_{50}$/ml; at use $1\times10^6$
A/Hawaii/15/01 $1\times10^{5.5}$ $TCID_{50}$/ml; at use $1\times10^{3.5}$
A/New Caledonia/12/99 $1\times10^{5.5}$ $TCID_{50}$/ml; at use $1\times10^{3.5}$ Positive control samples for the H3N2 Influenza A virus included:

VR 822 A/Victoria/3/75 $5\times10^{7.25}$ $TCID_{50}$/ml; at use $5\times10^{5.25}$
VR 547 A/Aichi/2/69 $5\times10^{5.5}$ $TCID_{50}$/ml; at use $5\times10^{3.5}$
A/Brazil/02/99 $1.9\times10^6$ $TCID_{50}$/ml; at use $1.9\times10^4$
A/New York/55/2004 $1\times10^5$ $TCID_{50}$/ml; at use $1\times10^3$
A/Hong Kong/2831/05 $1\times10^{5.5}$ $TCID_{50}$/ml; at use $1\times10^{3.5}$
A/Port Chalmers/1/73 $1\times10^{5.5}$ $TCID_{50}$/ml; at use $1\times10^{3.5}$
A/Hahmas/2696/99 $9.3\times10^7$ $TCID_{50}$/ml; at use $9.3\times10^5$
VR 544 A/Hong Kong/6/68 $5\times10^{5.75}$ $TCID_{50}$/ml; at use $5\times10^{3.75}$
A/California/07/04 $1\times10^{4.5}$ $TCID_{50}$/ml; at use $5\times10^{2.5}$
A/Hiroshima/53/05 $1\times10^5$ $TCID_{50}$/ml; at use $1\times10^3$
A/Fuijan/411/02 $1\times10^{5.5}$ $TCID_{50}$/ml; at use $1\times10^{3.5}$
A/Kentucky/03/06 $1\times10^{5.5}$ $TCID_{50}$/ml; at use $1\times10^{3.5}$
A/Costa Rica/07/99 $2\times10^7$$TCID_{50}$/ml; at use $2\times10^5$
A/Anhui/1239/05 $1\times10^{4.5}$ $TCID_{50}$/ml; at use $1\times10^{2.5}$
A/Victoria/512/05 $1\times10^5$ $TCID_{50}$/ml; at use $1\times10^3$ Note, strain VR 897 A/New Jersey/8/76 (HSW N1) is a recombinant H1N1 human and swine influenza A virus.

In addition, the primers and probes were tested against nucleic acids extracted from clinical samples from patients identified to have the 2009 H1N1 Influenza A virus.

Supermixes are generated for each of the primers and probes as described in Example 2. The concentrations of the primers and probes in the mixes may range from 50-500 nM. For instance, various primers or probes perform best at 50 nM, 75 nM, 100 nM, 150 nM, 200 nM, 250 nM, 300 nM, 350 nM, 400 nM, 450 nM, or 500 nM.

The PCR-based swine H1N1 influenza A virus, seasonal H1 influenza A virus assay, and seasonal H3 influenza A virus assays are performed by using primers and probes as described in Table 1-3 for real-time detection of the PCR amplicons. The reactions included an IC that is amplified and detected by using primers/probes specific to the internal control. Internal control sequences are known in the art. Additional positive controls are tested at the same time using the same conditions but using samples that contained known amounts of an H1N1 influenza A virus or H3N2 influenza A virus target.

The PCR-based seasonal H1 influenza A virus assay gave positive results for all tested samples that contained H1N1 influenza virus A nucleic acids and negative results for most of the control samples that contained H3N2 virus samples. Similarly, the PCR-based seasonal H3 influenza A virus assay gave positive results for all tested samples that contained H3N2 influenza A nucleic acids and negative results for all H1N1 influenza A control samples.

Sequences are eliminated from further study for various reasons including failure to react with their intended target (e.g., SEQ ID NO:10 and SEQ ID NO:32 probes do not react consistently well with the 2009 H1N1 influenza A strain target nucleic acids), and, because selective detection of H1N1, seasonal H1 or seasonal H3 was desired for this example, for cross reactivity to an unintended target nucleic acid (e.g., SEQ ID NO:40, SEQ ID NO: 41, and SEQ ID NO:49 react with the A/Kentucky/2/06 H1N1 strain). Other reasons to eliminate sequences were based on combinations of probes and primers which led to non-specific interactions, primer dimer formation, disparate primer amplification efficiencies or overall poor amplification, such with SEQ ID NO:53.

During the singleplex testing, 2 of the 27 mixes using primers and probes specific for the swine H1N1 influenza A virus did not react to the swine H1N1 influenza A virus test sample. Of the 25 primer/probe sets specific for the swine H1N1 influenza A virus, 2 of them reacted but had nonspecific amplification. 3 of the 11 primer/probe sets which targeted seasonal H3 Influenza A did not react and additional 1 of the 11 was eliminated for having an extremely late Ct.

Thus, 23 and 7 combinations of primers and probes specific for the swine H1N1 influenza A virus and seasonal H3 influenza A virus were found to be useful in a singleplex assay. Results from an Agilent BioAnalyzer gel showed that the H3N2 strain A/Kentucky/03/06 (#24) amplified with SEQ ID NOS:12 & 13 with 15 or 16 primers/probes at the correct size. The gel also showed that the seasonal H3 influenza A strain VR 822 A/Victoria/3/75 (#15) amplifies with the SEQ ID NOS:21 & 22 with 23, 24 or 25 primers/probe at the correct size. Strains VR 547 A/Aichi/2/69 (#16) and A/Costa Rica/07/99 (#22) amplify as well, but in triplicate, and not at the correct size, even though there is real time amplification.

The mixes of primers and probes were then optimized in the singleplex assay, by methods known to those of skill in the art, for example, by optimizing the concentration of the primer and/or probe in the mixture, by optimizing the amount of dNTPs used, through the addition of BSA or additional $MgCl_2$, or the amount of Taq Enzyme used.

EXAMPLE 4

Detection of Swine H1N1 Influenza A Virus in a Multiplex Reaction with Seasonal H1 Influenza A Virus and Optionally Seasonal H3 Influenza A Virus This example describes tests to determine whether the primers and probes selected from the singleplex tests above for specificity and selectivity were as effective if used in a multiplex reaction with primers, probes, and reagents for seasonal H1 Influenza A and possibly seasonal H3 Influenza A.

PCR-based swine H1N1 assays were performed substantially as described in Example 2, using primers sets from Tables 1-3 to amplify target RNA transcripts and detecting the amplicons by using a fluorophore-labeled probes from Tables 1-3. However, mixes of primers and probes specific for the nucleotide sequence encoding swine H1N1 influenza A virus NP gene or swine H1N1 influenza A HA gene were combined with primers and probes specific for seasonal H1 Influenza A virus and optionally the seasonal H3 Influenza A virus.

Various primer/probe combinations are eliminated based on this multiplex testing. For instance, when SEQ ID NO:45, SEQ ID NO:46, and SEQ ID NO:48 were tested in combination with SEQ ID NO:72, SEQ ID NO:73 and SEQ ID NO:74 (quencher in the middle of the probe), and SEQ ID NO:99, SEQ ID NO:100, and SEQ ID NO:102, and the Internal Control, there was a non specific amplification channel with water, poor sensitivity for seasonal H3 Influenza A virus strains (detected 1/3 dilutions), poor sensitivity for the seasonal H1 Influenza A virus strains (detected 1/3) and poor sensitivity for the swine H1N1 influenza A virus strains (detected 1/3). Similar sensitivity issues were found for the SEQ ID NO:50, SEQ ID NO:51, and SEQ ID NO:52 probe/primer set. Likewise, with primers and probes designed to be specific for the seasonal H3 Influenza A virus, certain probes when used in combination with specific primers and probes targeting seasonal H1 influenza A virus nucleic acids or specific primers and probes targeting swine H1N1 influenza A virus nucleic acids were not sufficiently sensitive, or selective enough for them to provide a robust signal in the multiplex format, for example, SEQ ID NOS: 94, 98 and 102. These combinations of primer/probe sets are subsequently eliminated from further study.

Once the primers and probes are initially tested in the multiplex format, the positive samples are titrated down to identify primers and probes for detecting lowered doses of each of the virus types.

EXAMPLE 5

Detection of Influenza Virus in Clinical Samples

This example describes primer and probe combinations for use in a multiplex real-time RT-PCR assay to detect and differentiate between seasonal H1 Influenza A virus, seasonal H3 Influenza A virus, and swine H1N1 Influenza A virus. The assay detects the amplicons in real time and provides positive results for samples that contain the target influenza virus. Assays are performed substantially as described in Example 3, but using an aliquot of prepared clinical sample nucleic acid in place of the target influenza virus RNA transcripts.

Samples are taken from patients and stored in accordance with Examples 1 and 2. Assays are performed substantially as described in Example 3 using an aliquot of prepared clinical sample nucleic acid. Fluorescent labels are detected and Ct value indicated that a sample contained a given target nucleic acid.

Before any assays that evaluate the sensitivity and selectivity of the primer/probe combinations are performed, the samples are first tested using the CDC rRT-PCR Flu Panel (IVD) to detect seasonal influenza A/H1 and A/H3 or the CDC rRT-PCR Swine Flu Panel (EUA) to detect 2009 H1N1 influenza A virus. Each sample containing a known virus is tested independently using the PCR-based swine H1N1 influenza A virus, seasonal H1 Influenza A virus or the seasonal H3 Influenza A virus test with the same IC. Separate swine H1N1 influenza A virus, seasonal H1 Influenza A virus, and seasonal H3 Influenza A virus nucleic acid assays are performed simultaneously under the same conditions using positive control samples that contained the relevant virus targets. Exemplary multiplex mixes are described below (each also including primers and a probe to an internal control).

| Name | Primer/ Probe |
|---|---|
| Mixture 1: | |
| SEQ ID NO: 72 | Primer |
| SEQ ID NO: 73 | Primer |
| SEQ ID NO: 74 | Probe |
| SEQ ID NO: 77 | Primer |
| SEQ ID NO: 78 | Primer |
| SEQ ID NO: 79 | Probe |
| SEQ ID NO: 1 | Primer |
| SEQ ID NO: 2 | Primer |
| SEQ ID NO: 4 | Probe |
| Mixture 2: | |
| SEQ ID NO: 72 | Primer |
| SEQ ID NO: 73 | Primer |
| SEQ ID NO: 74 | Probe |
| SEQ ID NO: 99 | Primer |
| SEQ ID NO: 100 | Primer |
| SEQ ID NO: 102 | Probe |
| SEQ ID NO: 42 | Primer |
| SEQ ID NO: 43 | Primer |
| SEQ ID NO: 44 | Probe |
| Mixture 3: | |
| SEQ ID NO: 72 | Primer |
| SEQ ID NO: 73 | Primer |
| SEQ ID NO: 74 | Probe |
| SEQ ID NO: 99 | Primer |
| SEQ ID NO: 100 | Primer |
| SEQ ID NO: 102 | Probe |
| SEQ ID NO: 26 | Primer |
| SEQ ID NO: 27 | Primer |
| SEQ ID NO: 29 | Probe |
| Mixture 4: | |
| SEQ ID NO: 72 | Primer |
| SEQ ID NO: 73 | Primer |
| SEQ ID NO: 74 | Probe |
| SEQ ID NO: 99 | Primer |
| SEQ ID NO: 100 | Primer |
| SEQ ID NO: 102 | Probe |
| SEQ ID NO: 54 | Primer |
| SEQ ID NO: 55 | Primer |
| SEQ ID NO: 57 | Probe |
| Mixture 5: | |
| SEQ ID NO: 72 | Primer |
| SEQ ID NO: 73 | Primer |
| SEQ ID NO: 74 | Probe |
| SEQ ID NO: 99 | Primer |
| SEQ ID NO: 100 | Primer |
| SEQ ID NO: 102 | Probe |
| SEQ ID NO: 1 | Primer |
| SEQ ID NO: 2 | Primer |
| SEQ ID NO: 4 | Probe |
| Mixture 6: | |
| SEQ ID NO: 72 | Primer |
| SEQ ID NO: 73 | Primer |
| SEQ ID NO: 74 | Probe |
| SEQ ID NO: 92 | Primer |
| SEQ ID NO: 93 | Primer |
| SEQ ID NO: 94 | Probe |
| SEQ ID NO: 17 | Primer |
| SEQ ID NO: 18 | Primer |
| SEQ ID NO: 20 | Probe |
| Mixture 7: | |
| SEQ ID NO: 72 | Primer |
| SEQ ID NO: 73 | Primer |
| SEQ ID NO: 74 | Probe |
| SEQ ID NO: 92 | Primer |
| SEQ ID NO: 93 | Primer |

-continued

| Name | Primer/ Probe |
|---|---|
| SEQ ID NO: 94 | Probe |
| SEQ ID NO: 12 | Primer |
| SEQ ID NO: 13 | Primer |
| SEQ ID NO: 15 | Probe |
| Mixture 8: | |
| SEQ ID NO: 72 | Primer |
| SEQ ID NO: 73 | Primer |
| SEQ ID NO: 74 | Probe |
| SEQ ID NO: 92 | Primer |
| SEQ ID NO: 93 | Primer |
| SEQ ID NO: 94 | Probe |
| SEQ ID NO: 12 | Primer |
| SEQ ID NO: 13 | Primer |
| SEQ ID NO: 16 | Probe |
| Mixture 9: | |
| SEQ ID NO: 72 | Primer |
| SEQ ID NO: 73 | Primer |
| SEQ ID NO: 74 | Probe |
| SEQ ID NO: 92 | Primer |
| SEQ ID NO: 93 | Primer |
| SEQ ID NO: 94 | Probe |
| SEQ ID NO: 21 | Primer |
| SEQ ID NO: 22 | Primer |
| SEQ ID NO: 23 | Probe |
| Mixture 10: | |
| SEQ ID NO: 72 | Primer |
| SEQ ID NO: 73 | Primer |
| SEQ ID NO: 74 | Probe |
| SEQ ID NO: 92 | Primer |
| SEQ ID NO: 93 | Primer |
| SEQ ID NO: 94 | Probe |
| SEQ ID NO: 21 | Primer |
| SEQ ID NO: 22 | Primer |
| SEQ ID NO: 25 | Probe |
| Mixture 11: | |
| SEQ ID NO: 72 | Primer |
| SEQ ID NO: 73 | Primer |
| SEQ ID NO: 74 | Probe |
| SEQ ID NO: 96 | Primer |
| SEQ ID NO: 97 | Primer |
| SEQ ID NO: 98 | Probe |
| SEQ ID NO: 17 | Primer |
| SEQ ID NO: 18 | Primer |
| SEQ ID NO: 20 | Probe |
| Mixture 12: | |
| SEQ ID NO: 72 | Primer |
| SEQ ID NO: 73 | Primer |
| SEQ ID NO: 74 | Probe |
| SEQ ID NO: 96 | Primer |
| SEQ ID NO: 97 | Primer |
| SEQ ID NO: 98 | Probe |
| SEQ ID NO: 12 | Primer |
| SEQ ID NO: 13 | Primer |
| SEQ ID NO: 15 | Probe |
| Mixture 13: | |
| SEQ ID NO: 72 | Primer |
| SEQ ID NO: 73 | Primer |
| SEQ ID NO: 74 | Probe |
| SEQ ID NO: 96 | Primer |
| SEQ ID NO: 97 | Primer |
| SEQ ID NO: 98 | Probe |
| SEQ ID NO: 12 | Primer |
| SEQ ID NO: 13 | Primer |
| SEQ ID NO: 16 | Probe |
| Mixture 14: | |
| SEQ ID NO: 72 | Primer |
| SEQ ID NO: 73 | Primer |
| SEQ ID NO: 74 | Probe |
| SEQ ID NO: 96 | Primer |

-continued

| Name | Primer/ Probe |
|---|---|
| SEQ ID NO: 97 | Primer |
| SEQ ID NO: 98 | Probe |
| SEQ ID NO: 21 | Primer |
| SEQ ID NO: 22 | Primer |
| SEQ ID NO: 23 | Probe |
| Mixture 15: | |
| SEQ ID NO: 72 | Primer |
| SEQ ID NO: 73 | Primer |
| SEQ ID NO: 74 | Probe |
| SEQ ID NO: 96 | Primer |
| SEQ ID NO: 97 | Primer |
| SEQ ID NO: 98 | Probe |
| SEQ ID NO: 21 | Primer |
| SEQ ID NO: 22 | Primer |
| SEQ ID NO: 25 | Probe |
| Mixture 16: | |
| SEQ ID NO: 72 | Primer |
| SEQ ID NO: 73 | Primer |
| SEQ ID NO: 74 | Probe |
| SEQ ID NO: 99 | Primer |
| SEQ ID NO: 100 | Primer |
| SEQ ID NO: 102 | Probe |
| SEQ ID NO: 17 | Primer |
| SEQ ID NO: 18 | Primer |
| SEQ ID NO: 20 | Probe |
| Mixture 17: | |
| SEQ ID NO: 72 | Primer |
| SEQ ID NO: 73 | Primer |
| SEQ ID NO: 74 | Probe |
| SEQ ID NO: 99 | Primer |
| SEQ ID NO: 100 | Primer |
| SEQ ID NO: 102 | Probe |
| SEQ ID NO: 12 | Primer |
| SEQ ID NO: 13 | Primer |
| SEQ ID NO: 15 | Probe |
| Mixture 18: | |
| SEQ ID NO: 72 | Primer |
| SEQ ID NO: 73 | Primer |
| SEQ ID NO: 74 | Probe |
| SEQ ID NO: 99 | Primer |
| SEQ ID NO: 100 | Primer |
| SEQ ID NO: 102 | Probe |
| SEQ ID NO: 12 | Primer |
| SEQ ID NO: 13 | Primer |
| SEQ ID NO: 16 | Probe |
| Mixture 19: | |
| SEQ ID NO: 72 | Primer |
| SEQ ID NO: 73 | Primer |
| SEQ ID NO: 74 | Probe |
| SEQ ID NO: 99 | Primer |
| SEQ ID NO: 100 | Primer |
| SEQ ID NO: 102 | Probe |
| SEQ ID NO: 21 | Primer |
| SEQ ID NO: 22 | Primer |
| SEQ ID NO: 23 | Probe |
| Mixture 20: | |
| SEQ ID NO: 72 | Primer |
| SEQ ID NO: 73 | Primer |
| SEQ ID NO: 74 | Probe |
| SEQ ID NO: 99 | Primer |
| SEQ ID NO: 100 | Primer |
| SEQ ID NO: 102 | Probe |
| SEQ ID NO: 21 | Primer |
| SEQ ID NO: 22 | Primer |
| SEQ ID NO: 25 | Probe |
| Mixture 21: | |
| SEQ ID NO: 72 | Primer |
| SEQ ID NO: 73 | Primer |
| SEQ ID NO: 74 | Probe |

-continued

| Name | Primer/ Probe |
|---|---|
| SEQ ID NO: 99 | Primer |
| SEQ ID NO: 100 | Primer |
| SEQ ID NO: 102 | Probe |
| SEQ ID NO: 26 | Primer |
| SEQ ID NO: 27 | Primer |
| SEQ ID NO: 28 | Probe |

Results are obtained by measuring the Ct and/or RFU corresponding to each of the fluorescent signals as described above for each target strain.

Exemplary results: For mixture 1 the following results are obtained for the various target strains. Of the 168 samples tested, 24 samples are known to be positive for seasonal H1 Influenza A virus, the multiplex assay detected 23 of these samples. Of the 168 samples tested, 20 are known to be positive for the Seasonal H3 Influenza A virus, and all 20 are detected. Likewise, 52 of the 168 samples are known to be positive for swine H1N1 Influenza A. The assay detects 50 of those samples.

The invention being thus described, it will be apparent to one of ordinary skill in the art that various modifications of the materials and methods for practicing the invention can be made. Such modifications are to be considered within the scope of the invention as defined by the following claims.

Each of the references from the patent and periodical literature cited herein is hereby expressly incorporated in its entirety by such citation.

I claim:

1. A composition comprising:

at least first and second seasonal H1 influenza A-specific amplification primers, wherein the first primer comprises a H1 influenza A-specific sequence consisting of SEQ ID NO:72 and the second primer comprises a H1 influenza A-specific sequence consisting of SEQ ID:73; and a seasonal H1 influenza A-specific oligonucleotide detection probe having a H1 influenza A-specific sequence of at least 18 contiguous nucleotides, wherein said detection probe is complementary to a H1 influenza A nucleic acid sequence that is amplifiable by the first and second primers, and wherein said detection probe comprises at least a first detectable label operably linked to said oligonucleotide detection probe.

2. The composition according to claim 1, wherein at least one of said nucleic acid primers or said probe includes one or more nucleotides at the 5' end that are not specific for H1 influenza A nucleic acid, and wherein said nucleic acid primers and said probe are no more than 50 nucleotides in length.

3. The composition according to claim 1, wherein said first and second primers are SEQ ID NO:72 and SEQ ID NO:73,respectively and the H1 influenza A-specific sequence of said probe is SEQ ID NO:74.

4. A kit comprising the composition according to claim 3.

5. The composition of claim 1, wherein said first and second primers are SEQ ID NO:72 and SEQ ID NO:73, respectively.

6. The composition of claim 5, wherein the H1 influenza A-specific sequence of said probe is selected from the group consisting of SEQ ID NO:74, SEQ ID NO:75, and SEQ ID NO:76.

7. A kit comprising, in a suitable container, a composition according to claim 6, and instructions for use of said composition in any assay for amplification of polynucleotides in a biological sample.

8. A kit comprising a composition according to claim 1.

9. The kit according to claim 8, wherein the kit further comprises instructions for use of said composition in any assay for amplification of polynucleotides in a biological sample.

* * * * *